(12) United States Patent
Fan et al.

(10) Patent No.: US 12,419,596 B2
(45) Date of Patent: Sep. 23, 2025

(54) SYSTEMS AND METHODS FOR COMPUTED TOMOGRAPHY

(71) Applicant: GE Precision Healthcare LLC, Wauwatosa, WI (US)

(72) Inventors: Jiahua Fan, New Berlin, WI (US); Changlyong Kim, Brookfield, WI (US); Ming Yan, Waukesha, WI (US); Scott D. Slavic, Sussex, WI (US); Jiang Hsieh, Brookfield, WI (US); Nicholas R. Konkle, Sussex, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 578 days.

(21) Appl. No.: 17/815,186

(22) Filed: Jul. 26, 2022

(65) Prior Publication Data

US 2024/0032879 A1 Feb. 1, 2024

(51) Int. Cl.
| | | |
|---|---|---|
| *A61B 6/42* | (2024.01) | |
| *A61B 6/00* | (2006.01) | |
| *A61B 6/46* | (2024.01) | |
| *G06T 3/4046* | (2024.01) | |
| *G06T 11/00* | (2006.01) | |

(52) U.S. Cl.
CPC .......... *A61B 6/4266* (2013.01); *A61B 6/4233* (2013.01); *A61B 6/4241* (2013.01); *A61B 6/463* (2013.01); *A61B 6/5235* (2013.01); *A61B 6/5258* (2013.01); *A61B 6/56* (2013.01); *G06T 3/4046* (2013.01); *G06T 11/008* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 7,372,934 B2 | 5/2008 | De Man et al. | |
| 7,968,853 B2 | 6/2011 | Altman et al. | |
| 9,678,220 B2 | 6/2017 | Herrmann | |
| 10,143,417 B2* | 12/2018 | Danielsson | ............ A61B 6/505 |

(Continued)

OTHER PUBLICATIONS

EP application 23185501.6 filed Jul. 14, 2023—extended Search Report issued Nov. 28, 2023, 12 pages.

(Continued)

*Primary Examiner* — Anand P Bhatnagar
(74) *Attorney, Agent, or Firm* — McCoy Russell LLP

(57) ABSTRACT

Systems and methods are provided for increasing a quality of computed tomography (CT) images. In one embodiment, a computed tomography (CT) detector system comprises a layer of energy integrating detectors (EID) arranged below a layer of photon counting (PC) sensors with respect to an incoming x-ray, where a number of the PC sensors exceeds a number of the EID detectors; and an image processing unit configured to correct PC data using EID data, and denoise and increase a resolution of an image reconstructed from EID data and PC data using a deep learning convolutional neural network (CNN) trained on pairs of images, each pair of images including a target image reconstructed from a first signal from the layer of PC sensors, and an input image reconstructed from a second signal from the layer of EID detectors, the EID data and PC data acquired concurrently from a same patient ray path.

19 Claims, 8 Drawing Sheets

(56) References Cited

U.S. PATENT DOCUMENTS

| | | | |
|---|---|---|---|
| 10,176,603 B2* | 1/2019 | Rigie | G06T 5/73 |
| 10,575,801 B2* | 3/2020 | Danielsson | G01T 1/17 |
| 10,667,774 B2* | 6/2020 | Kato | A61B 6/4233 |
| 10,813,607 B2* | 10/2020 | Bakowski Holtryd | A61B 6/4241 |
| 11,726,215 B2* | 8/2023 | Sjölin | G01T 1/247 250/370.09 |
| 2007/0147574 A1 | 6/2007 | Bernard De Man et al. | |
| 2007/0205367 A1 | 9/2007 | Deman | |
| 2008/0210877 A1 | 9/2008 | Altman et al. | |
| 2009/0129538 A1* | 5/2009 | Tkaczyk | G01T 1/249 250/361 R |
| 2010/0215230 A1* | 8/2010 | Bornefalk | G01T 1/366 382/128 |
| 2015/0223766 A1* | 8/2015 | Besson | G01T 1/2985 378/62 |
| 2018/0042562 A1* | 2/2018 | Danielsson | A61B 6/4035 |
| 2021/0378611 A1* | 12/2021 | De Man | A61B 6/0407 |

OTHER PUBLICATIONS

JP application 2023-110486 filed Jul. 5, 2023—Office Action issued Jul. 3, 2024; Machine Translation; 6 pages.

Eng, S. et al., "Photon-counting Detector CT: System Design and Clinical Applications of an Emerging Technology," Radiographics, vol. 39, No. 3, May 2019, 15 pages.

* cited by examiner

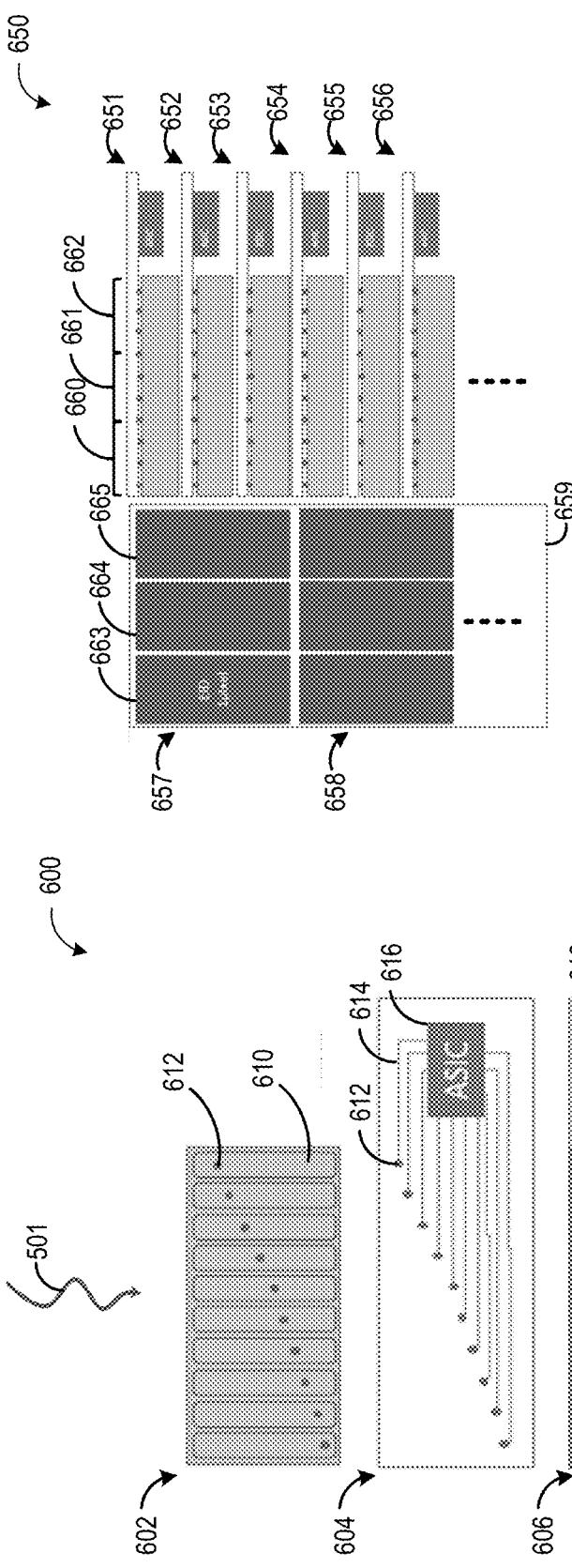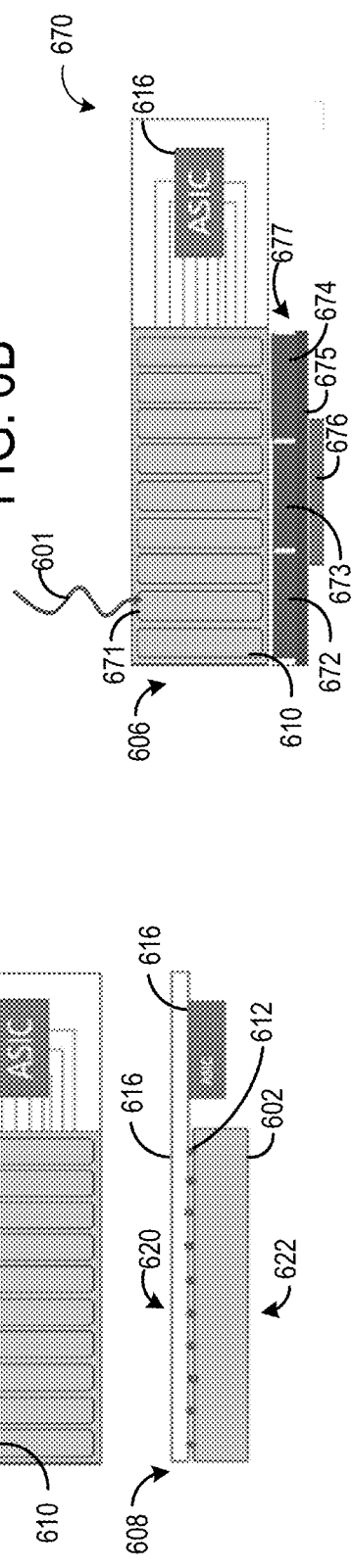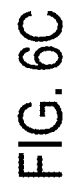
FIG. 6B
FIG. 6C
FIG. 6A

SYSTEMS AND METHODS FOR COMPUTED TOMOGRAPHY

TECHNICAL FIELD

Embodiments of the subject matter disclosed herein relate to medical imaging, and more particularly, to increasing a quality of images reconstructed using computerized tomography imaging systems.

BACKGROUND

In computed tomography (CT) imaging systems, an electron beam generated by a cathode is directed towards a target within an x-ray tube. A fan-shaped or cone-shaped beam of x-rays produced by electrons colliding with the target is directed towards a subject, such as a patient. After being attenuated by the object, the x-rays impinge upon an array of radiation detectors, generating an image.

A quality of a CT image may be increased by using Photon Counting CT (PCCT), where the radiation detectors are photon-counting detectors, and photons are counted to provide spectral information. PCCT uses a direct-conversion detector and has various advantages over conventional indirect-conversion-detector-based Energy Integrating Detector (EID) CT systems. However, with a PCCT system, photon pile-up may occur at higher input count rates due to a limited capability of the photon-counting detectors, which reduces image quality at a high x-ray flux rate. Smaller detector pixels may be introduced to reduce the pile-up effect. However, reducing a size of the detector pixels may increase a number of channels used, increasing both power consumption and data size. Smaller pixels may introduce more charge sharing among channels due to closer proximity, and gaps between detector modules may become comparable to the detector pixel size. Additionally, there may be more low performance pixels.

SUMMARY

The current disclosure at least partially addresses one or more of the above identified issues by a CT detector system comprising a layer of energy integrating detectors (EID) arranged at an opposite side of a layer of photon counting (PC) sensors with respect to an incoming x-ray, where a number of the PC sensors exceeds a number of the EID detectors. The CT detector system may further include an image processing unit configured to correct PC data using EID data, and denoise and increase a resolution of an image reconstructed from EID data and PC data using a deep learning convolutional neural network (CNN) trained on pairs of images, each pair of images including a target image reconstructed from a first signal from the layer of PC sensors, and an input image reconstructed from a second signal from the layer of EID detectors, the EID data and PC data acquired concurrently from a same patient ray path. By using a multi-layer CT detector including the layer of EID detectors (e.g., a two-dimensional EID detector array) and a layer of PC sensors (e.g., a two-dimensional PC sensor array), advantages of both PC detectors and EID detectors may be leveraged to achieve higher image quality than may be achieved by either detector type alone for various clinical CT applications. By arranging the layer of PC sensors between the layer of EID detectors and an x-ray source, a size of the PC sensors may be reduced compared to traditional PCCT detector systems, which may reduce the effects of photon pile-up, increasing a resolution and decreasing an amount of noise in an image reconstructed from both PC data and EID data rather than either PC data or EID data alone.

Additionally, by including PC sensors and EID detectors that are different sizes, and therefore not perfectly aligned, gaps between PC sensors may be compensated for by the EID detectors. In other words, a photon that falls in a gap and is not counted at the PC sensor array may be detected by an EID detector positioned underneath the gap, such that all the photons of an incoming x-ray may be detected by either the PC sensors or the EID detectors. In turn, an increased resolution and decreased amount of noise in an image reconstructed from both PC data and EID data results as compared to using only one of PC data or EID data. Moreover, this arrangement may reduce a reliance on a slanted configuration that is currently implemented. A slanted edge forces the shape of each detector element to deviate from a rectangular shape. Since, in non-symmetrical shape, the geometrical center of a detector element is different from the signal weighted center, it is difficult to assign its proper geometrical location and hard to align their counter parts in the neighboring detector modules. Further, since the pile-up issue is avoided with the EID detectors, and sensor response is linear to an incoming x-ray flux, EID data can be used to guide a pile-up correction to the PC sensor data, resulting in more accurate pile-up corrections and greater resolution.

An additional advantage of the proposed multi-layer CT detector is that a cost of silicon chips used in the PC sensors may be reduced. Silicon has been demonstrated to have superior spectral response and is a good candidate for a PC sensor. However, a depth of the silicon used in a PC sensor may have to be greater than a depth of an alternative semiconductor material, to ensure good dose efficiency and correctible pileup amount. However, because some of the x-ray photons penetrating the CT detector may be allowed to pass through the PC sensors and enter the EID detectors, and because pile-up can be more accurately corrected using the EID data, the depth of the silicon may be reduced, thereby reducing a cost and data size (less segments and channels) of the CT detector. A power consumption and a thermal dissipation of the CT detector may also be reduced.

Further, EID data can be used alone to generate conventional kVp images when fast throughput is desired and conventional CT images are desired, as opposed to images reconstructed based on photon counts. Since EID data projections are highly filtered by the PC sensor layer, a narrower energy spectrum is expected, which translates to an improved beam-hardening performance if images are reconstructed from EID data projections alone.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 6A is a schematic diagram of components of a two-dimensional PC sensor array of a multi-layer CT detector, in accordance with one or more embodiments of the present disclosure;

FIG. 6B is a schematic diagram showing an alignment of a plurality of two-dimensional PC sensor arrays of a multi-layer CT detector with a plurality of EID detectors in an underlying EID detector layer, in accordance with one or more embodiments of the present disclosure;

FIG. 6C is a schematic diagram showing the configuration of PC sensor arrays and EID detectors of FIG. 6B from a different perspective, in accordance with one or more embodiments of the present disclosure;

Figure 1:
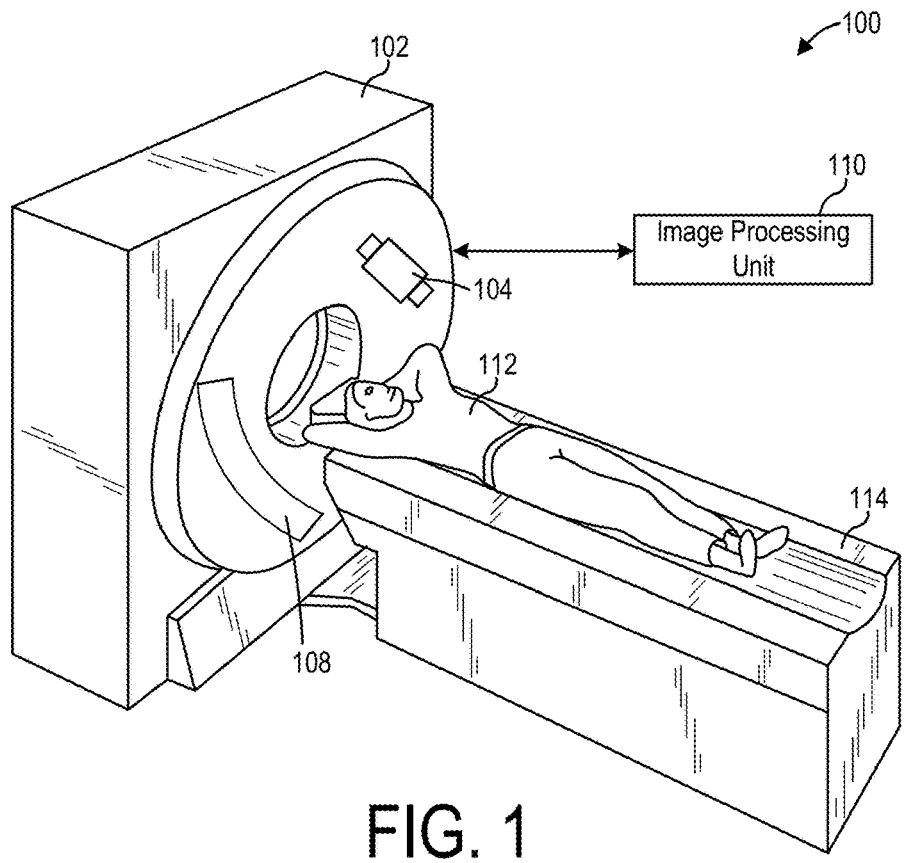
FIG. 1 shows a pictorial view of an imaging system, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for increasing a quality of images acquired via a photon-counting computed tomography (PCCT) system. Typically, in computed tomography (CT) imaging systems, an x-ray source emits a fan-shaped beam or a cone-shaped beam towards an object, such as a patient. Generally, in CT systems the x-ray source and the detector array are rotated about a gantry within an imaging plane and around the patient, and images are generated from projection data at a plurality of views at different view angles. For example, for one rotation of the x-ray source, 1000 views may be generated by the CT system. The beam, after being attenuated by the patient, impinges upon an array of radiation detectors. The x-ray detector or detector array typically includes a collimator for collimating x-ray beams received at the detector, a scintillator disposed adjacent to the collimator for converting x-rays to light energy, and photodiodes for receiving the light energy from the adjacent scintillator and producing electrical signals therefrom. An intensity of the attenuated beam radiation received at the detector array is typically dependent upon the attenuation of the x-ray beam by the patient. Each detector element of a detector array produces a separate electrical signal indicative of the attenuated beam received by each detector element. The electrical signals are transmitted to a data processing system for analysis. The data processing system processes the electrical signals to facilitate generation of an image.

Such conventional CT imaging systems utilize detectors that convert radiographic energy into current signals that are integrated over a time period, then measured and ultimately digitized. However, a drawback of such detectors is their inability to provide data or feedback as to the number and/or energy of photons detected. That is, the light emitted by the scintillator is a function of both a number of x-rays impinged and an energy level of the x-rays. The photodiodes may not be capable of discriminating between the energy level or the photon count from the scintillation. For example, two scintillators may illuminate with equivalent intensity and, as such, provide equivalent output to their respective photodiodes. Yet, despite yielding an equivalent light output, the number of x-rays received by each scintillator may be different, and an intensity of the x-rays may be different.

In contrast, PCCT detectors may provide photon counting and/or energy discriminating feedback with high spatial resolution. PCCT detectors can be caused to operate in an x-ray counting mode, an energy measurement mode of each x-ray event, or both. While a number of materials may be used in the construction of a hybrid photon counting energy discriminating detector, semiconductors have been shown to be one preferred material. Typical materials for such use include Cadmium Zinc Telluride (CZT), Cadmium Telluride (CdTe) and Silicon (Si), which may have a cost-effective production capability. Other heavy semiconductors, thallium bromide (TlBr), mercury iodide (HgI), etc. can be used when they can be produced cost effectively in large volume.

PCCT detectors support not only x-ray photon counting, but energy measurement or tagging as well, supporting the acquisition of both anatomical detail as well as tissue characterization information. In this regard, energy discriminating information or data may be used to reduce the effects of beam hardening and the like. Furthermore, these detectors support the acquisition of tissue discrimination data and therefore provide diagnostic information that is indicative of disease or other pathologies. PCCT detectors can also be used to detect, measure, and characterize materials that may be injected into a subject, such as contrast agents and/or other specialized materials, by the use of optimal energy weighting to boost the contrast of iodine and calcium (and other high atomic-number materials). Contrast agents can, for example, include iodine that is injected into the blood stream for better visualization.

A drawback of direct conversion semiconductor detectors, however, is that these types of detectors cannot count at the x-ray photon fluxes typically encountered with conventional CT systems. Saturation can occur at detector locations wherein small subject thickness is interposed between the detector and the radiographic energy source or x-ray tube. These saturated regions correspond to paths of low subject thickness near or outside the width of the subject projected onto the detector fan-arc. In many instances, the subject is more or less circular or elliptical in the effect on attenuation of the x-ray flux and subsequent incident intensity to the detector. In this case, the saturated regions represent two disjointed regions at extremes of the fan-arc. In other less typical, but not rare instances, saturation occurs at other locations and in more than two disjointed regions of the detector.

Pile-up is a phenomenon that occurs with PCCT detectors when a source flux at the detector is so high that there is a non-negligible possibility that two or more x-ray photons deposit charge packets in a single pixel close enough in time so that their signals interfere with each other. Pile-up phenomenon are of two general types, which result in somewhat different effects. In the first type, the two or more events are separated by sufficient time so that they are recognized as distinct events, but the signals overlap so that the precision of the measurement of the energy of the later arriving x-ray or both x-rays is degraded. This type of pile-up results in a degradation of the energy resolution of the system. In the second type of pile-up, the two or more events arrive close enough in time so that the system is not able to resolve them as distinct events. In such a case, these events are recognized as one single event having the sum of their energies and the events are shifted in the spectrum to higher energies. In addition, pile-up leads to a more or less pronounced depression of counts in high x-ray flux, resulting in detector quantum efficiency (DQE) loss.

This pile-up may lead to detector saturation, which occurs at a relatively low x-ray flux level in direct conversion sensors. Above the level, the detector response is not predictable and has degraded dose utilization that leads to loss of imaging information and results in noise and artifacts in x-ray projection and CT images. In particular, photon counting, direct conversion detectors saturate due to the intrinsic charge collection time (i.e., charge drift time) associated with each x-ray photon event. Saturation will occur due to pulse pile-up when x-ray photon absorption rate for each pixel is on the order of the inverse of this charge collection time.

PCCT systems typically have one or more energy bins that are determined by a comparator that typically is part of a readout of a data acquisition system (DAS). For a one-bin system, typically one energy threshold of the comparator is set to an energy value that is high enough such that there are few or no false noise counts, but low enough such that there is little loss of signal x-rays in the readout process. Such a system is subject to statistical error and bias due to the pile-up of multiple energy events, as described.

A system having many energy bins may be formed with multiple comparators in the readout DAS. Each comparator may be set to trigger for photons above a set level of energy that results in accumulation on a register of the number of photons above a corresponding x-ray energy level. The bin counts may be weighted and added together to form a system output having specific information content appropriate for an imaging system. However, like a one-bin system, a multiple bin system is subject to degradation due to pile-up, resulting in DQE loss. The mean pile-up of bin counts may be corrected, but with a loss of statistical accuracy. The signal-to-noise ratio (SNR) may be used to assess the weighted sums for a system output.

In some embodiments, the sensors of a PCCT detector may be configured as a plurality of sensor segments within a sensor array, where the sensor segments are oriented in a direction of incoming x-rays. The sensor segments are used to prevent or account for pile-up behavior at the detector. The number of segments may be minimized to conserve channels to an application-specific integrated circuit (ASIC) electrically coupled to the sensor array, for analog/digital (A/D) conversion and readout. However, pile-up may still occur within the sensor segments.

As disclosed herein, the benefits of direct conversion detectors may be reaped while minimizing pile-up behavior and other drawbacks of PCCT systems by including both a PC detector and an EID detector. Specifically, a multi-layer detector configuration is disclosed herein, where an EID detector array is arranged in a layer below a PC sensor array. Readout electronics for the PC sensor array and/or the EID detector array may be arranged underneath the EID detector array, or on a side of the PC sensor array. For the purposes of this disclosure, underneath refers to a positioning of an element relative to an incoming x-ray, which is depicted vertically in FIGS. 4-6E with x-rays entering components of a CT detector in a vertically descending manner. Thus, a position of the EID detector array underneath or below the PC sensor array refers to a positioning of the EID detector array at an opposite side of the PC sensor array as an incoming x-ray, and a position of the readout electronics underneath or below the EID detector array refers to a positioning of the readout electronics at an opposite side of the EID detector array as an incoming x-ray (and the PC sensor array).

Measurements of photon counts in an x-ray path are taken both using the PC sensor array and the EID detector array, where EID data and PC data is acquired concurrently from a same patient ray path. To ensure that EID detector array will be able to get a sufficient signal, the PC sensor array may be configured not to capture all the photons in an x-ray beam. In other words, a stopping power of the PC detector may be optimized by a thickness that is expected to reduce pile-up in the PC detector. For example, the stopping power may be 40% (e.g., where 40% of the photons of the x-ray beam are detected at the PC sensor array, and 60% of the photons of the x-ray pass through the PC sensor array to be detected at the EID detector array. X-ray photons passing through the PC sensor array are captured by the EID detector array positioned underneath the PC sensor array. Both the PC sensors and the EID detectors may be used to generate spectral information as well as non-spectral information.

At least one advantage of the disclosed detector configuration is that in addition to reducing the pile-up behavior at the PC detector, EID data may be used to correct the pile-up behavior in the PC data, as described in greater detail below. In this way, advantages from both types of detectors may be leveraged to achieve better image quality for various clinical CT applications.

Figure 2:
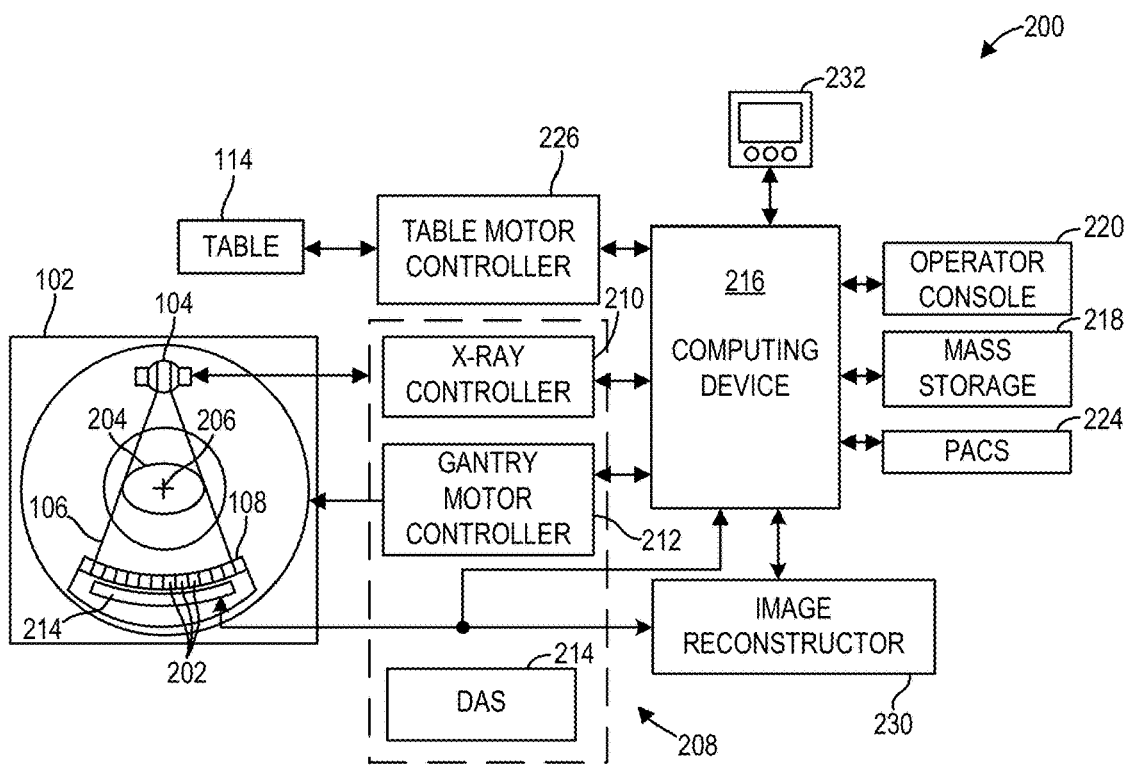
FIG. 2 shows a block schematic diagram of an exemplary imaging system, in accordance with one or more embodiments of the present disclosure.
Figure 3:
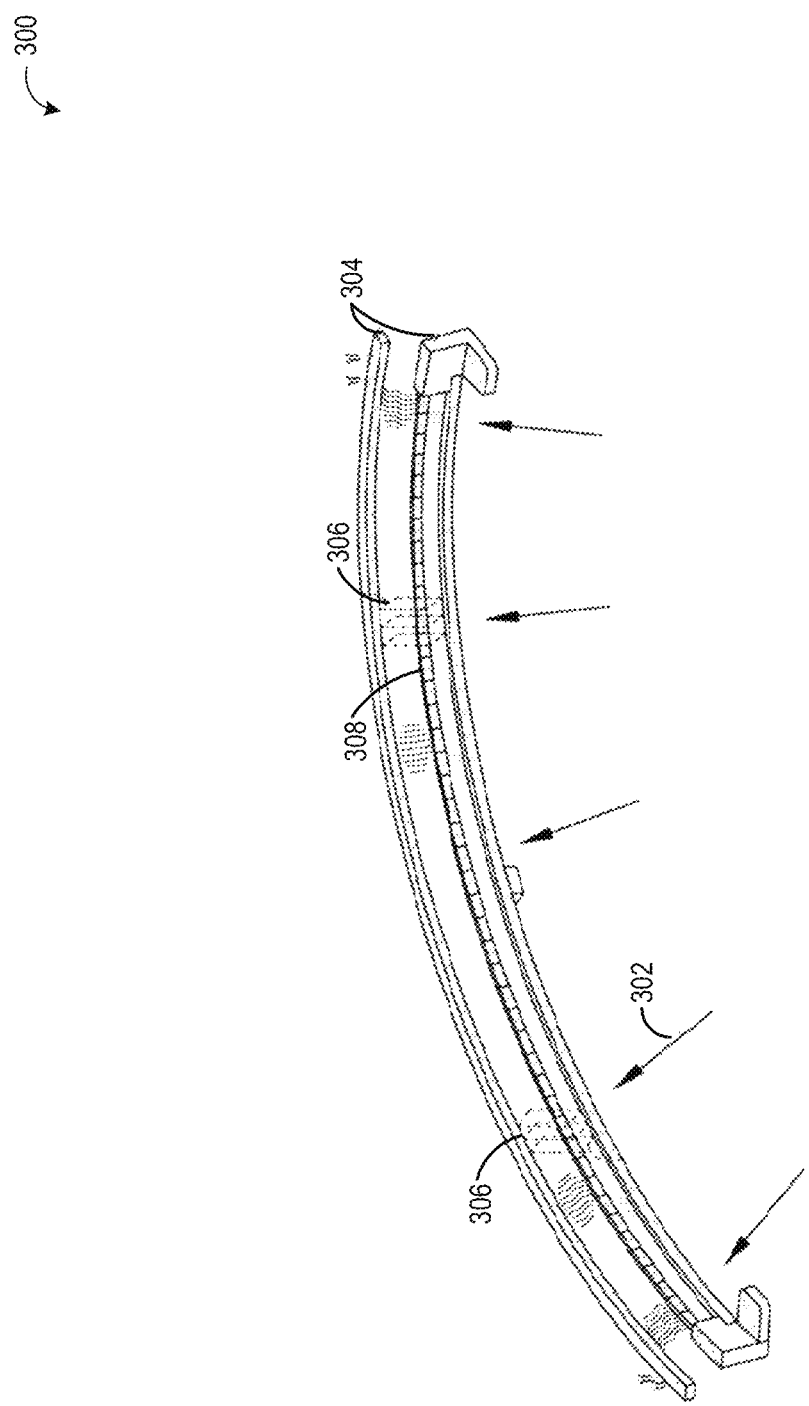
FIG. 3 is a schematic diagram of an exemplary detector array of a PCCT system, in accordance with one or more embodiments of the present disclosure.
Figure 4:
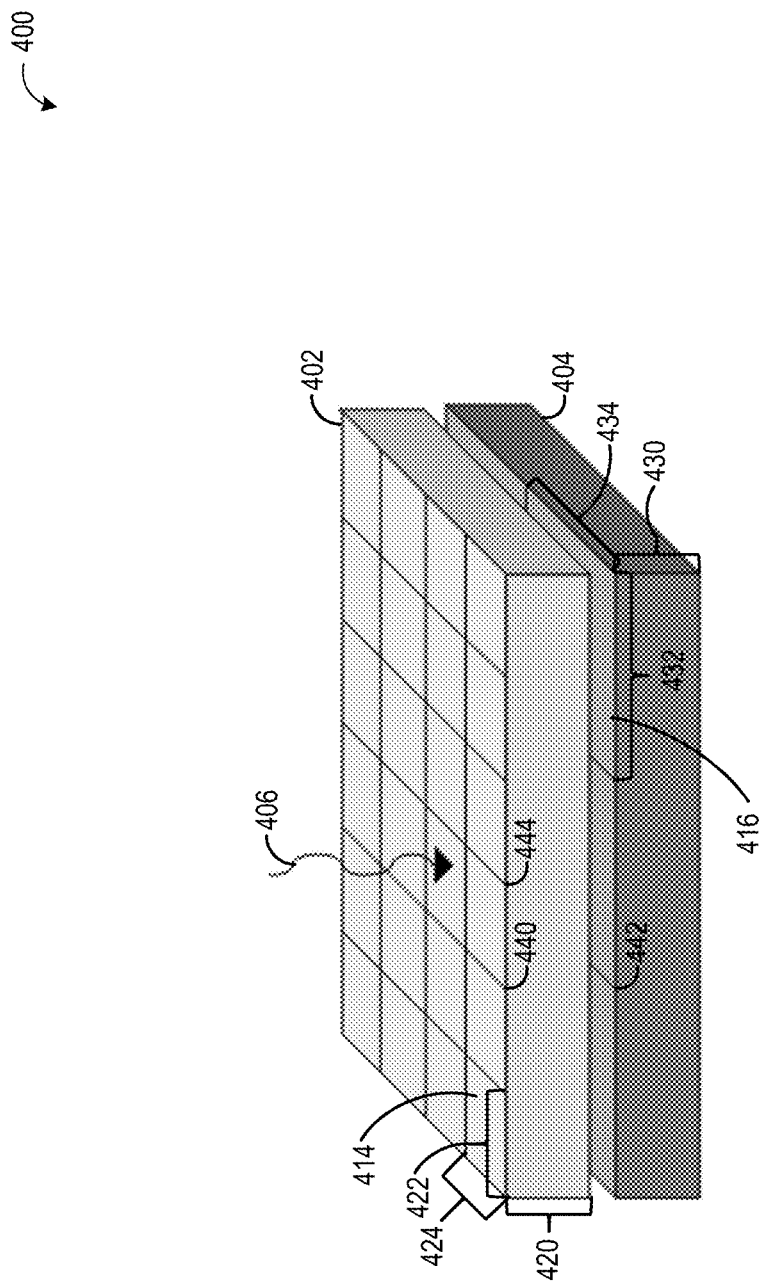
FIG. 4 shows x-rays directed at a multi-layer CT detector, in accordance with one or more embodiments of the present disclosure.
Figure 5A:
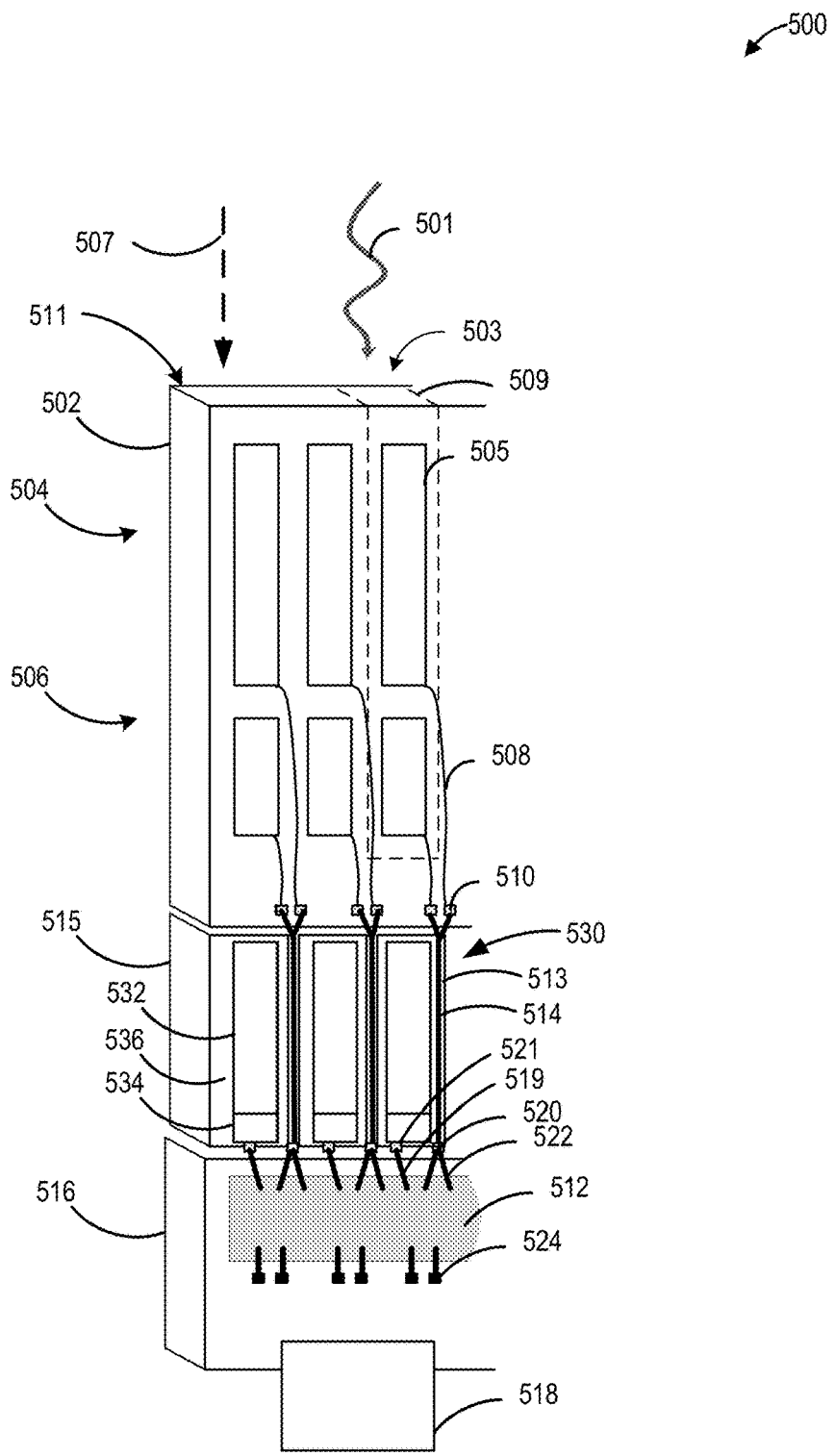
FIG. 5A is a schematic diagram of a multi-layer CT detector from a first perspective, in accordance with one or more embodiments of the present disclosure.
Figure 5B:
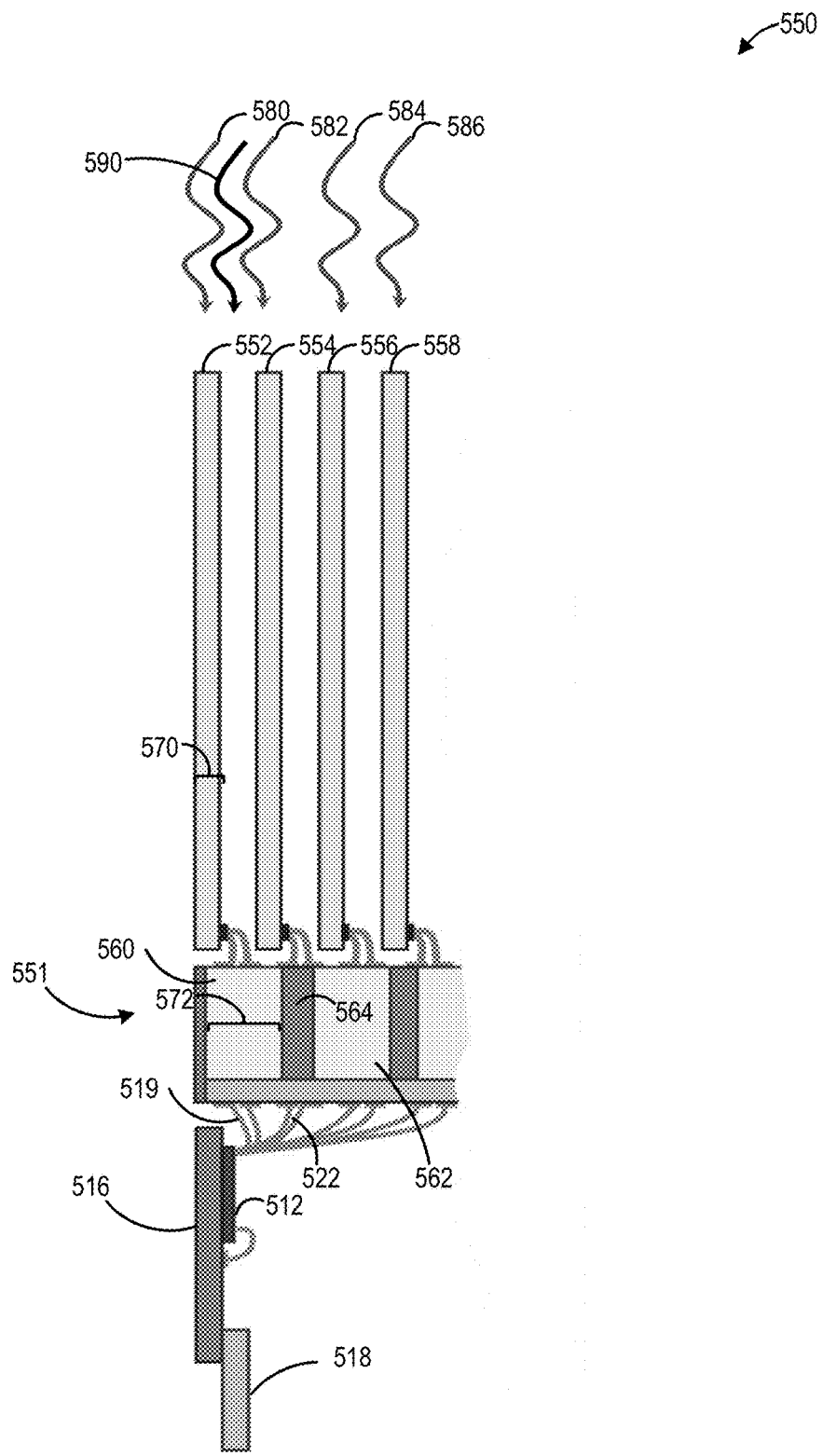
FIG. 5B is a schematic diagram of a multi-layer CT detector from a second perspective, in accordance with one or more embodiments of the present disclosure.
Figure 6D:
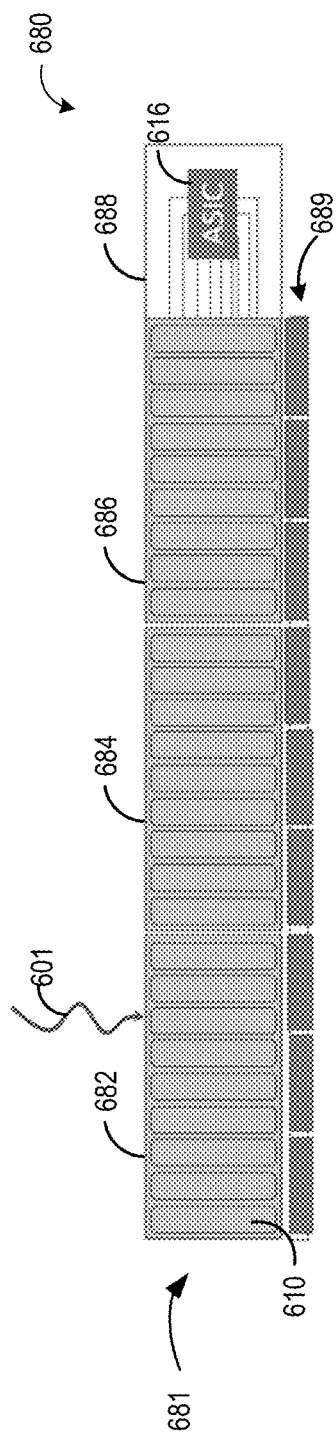
FIG. 6D is a schematic diagram showing a first alternative configuration of PC sensor arrays and EID detectors of a multi-layer CT detector, in accordance with one or more embodiments of the present disclosure.
Figure 6E:
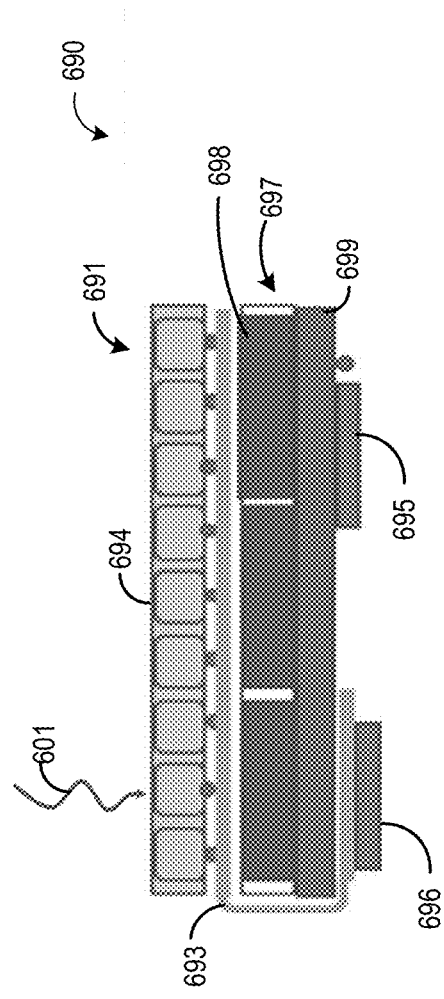
FIG. 6E is a schematic diagram showing a second alternative configuration of PC sensor arrays and EID detectors of a multi-layer CT detector, in accordance with one or more embodiments of the present disclosure.

An example of a PCCT system that may be used to perform contrast scans in accordance with the present techniques is provided in FIGS. 1 and 2. FIG. 3 shows an example CT detector array of the PCCT system, where photons of x-rays directed at a subject by an x-ray source are counted by PCCT detectors of a PCCT detector array. The detectors may be multi-layer CT detectors including a PC sensor layer and an EID detector layer, as shown in FIG. 4. Two perspective views of an exemplary multi-layer CT detector are shown in FIGS. 5A and 5B, where readout electronics for the PC sensor layer and an EID detector layer are positioned underneath the EID detector layer. In an alternative configuration of the multi-layer CT detector, a first readout electronics is used to count photons in the PC sensor layer may be positioned to a side of a PC sensor array, as shown in FIG. 6A. A plurality of PC sensor arrays may be superimposed above a plurality of EID detectors of the EID detector layer, as shown in FIG. 6B. A second readout electronics is used to measure energy of x-ray beams entering the EID detector layer may be positioned underneath the EID detector layer, as shown in FIG. 6C. A PC sensor array may include a plurality of PC sensors on a plurality of silicon chips, where each PC sensor may be electronically coupled to the first readout electronics positioned to a side of a PC sensor array, as shown in FIG. 6D. In another alternative configuration, the first readout electronics may be positioned underneath the EID detector layer, where the plurality of PC sensors are electronically coupled to the first readout electronics via one or more flexible cables routed around the EID detector layer, as shown in FIG. 6E. A resolution of an image reconstructed from both PC data and EID data may be increased by following one or more steps of a method described in FIG. 7.

FIGS. 1-6E show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below/underneath one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 illustrates an exemplary PCCT system 100 configured for CT imaging with photon-counting detectors. Particularly, the PCCT system 100 is configured to image a subject 112 such as a patient, an inanimate object, one or more manufactured parts, and/or foreign objects such as dental implants, stents, and/or contrast agents present within the body. In one embodiment, the PCCT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts a single x-ray source 104, in certain embodiments, multiple x-ray sources and detectors may be employed to project a plurality of x-ray radiation beams for acquiring projection data at different energy levels corresponding to the patient. In some embodiments, the x-ray source 104 may enable dual-energy gemstone spectral imaging (GSI) by rapid peak kilovoltage (kVp) switching. In the embodiments described herein, the x-ray detector employed is a photon-counting detector which is capable of differentiating x-ray photons of different energies.

In certain embodiments, the PCCT system 100 further includes an image processing unit 110 configured to reconstruct images of a target volume of the subject 112 using an iterative or analytic image reconstruction method. For example, the image processing unit 110 may use an analytic image reconstruction approach such as filtered back projection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processing unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the x-ray beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector.

FIG. 2 illustrates an exemplary imaging system 200 similar to the PCCT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon-counting detectors which register the interactions of individual photons into one or more energy bins.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. It is noted that the computing device 216 may be the same or similar to image processing unit 110, in at least one example. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Referring now to FIG. 3, a CT detector array 300 is shown, which may be a non-limiting example of detector array 108 of FIG. 2. Detector array 300 includes rails 304 having collimating blades or plates 306 placed therebetween. Plates 306 are positioned to collimate x-rays 302 before such beams impinge upon a plurality of detectors 308 of detector array 300, which may be arranged between the plates 306. As an example, detector array 300 may include 57 detectors 308, each detector 308 having an array size of 64×16 of pixel elements. As a result, detector array 300 would have 64 rows and 912 columns (16×57 detectors), allowing for 64 simultaneous slices of data to be collected with each gantry rotation (e.g., the gantry 102 of FIG. 1).

As described in greater detail below, each CT detector 308 may be a multi-layer CT detector including both a PC sensor array configured to directly convert radiographic energy to electrical signals containing energy discriminatory or photon count data, and an EID detector array configured to indirectly convert radiographic energy to electrical signals via photodiodes receiving the light energy from adjacently positioned scintillators.

FIG. 4 shows a proposed multi-layer CT detector configuration 400, including a PC sensor array 402 arranged in a top layer, and an EID detector array 404 arranged in a bottom layer (e.g., underneath PC sensor array 402), with respect to an x-ray 406. PC sensor array 402 is a two-dimensional sensor array comprising a first number M of PC sensors, and EID detector array 404 is two-dimensional sensor array comprising a second number N of EID detectors, where M may be greater than N. As a result of M being greater than N, the PC sensors may be of a first size (e.g., length and width), and the EID detectors may be of a second size, where the second size is different from the first size. For example, a PC sensor 414 of the first number M of PC sensors may have a first length 422 and a first width 424. An EID detector 416 of the second number N of EID detectors of may have a second length 432 and second width 434, where second length 432 and second width 434 are greater than first length 422 and first width 424.

The difference in size between each PC sensor and each EID detector may contribute to a higher quality reconstructed image. If M=N, the length and width of each sensor used for both M and N is the same. If the size of both the PC sensor and EID detector is small, the EID detectors may have large dose efficiency issue. If the size of both the PC sensor and EID detector is large, the PC sensors will suffer from severe pile-up problem. With M>N, a good pile-up correction, high spatial resolution and good dose efficiency may be achieved at the same time.

PC sensor 414 may have a first height 420, and EID detector 416 may have a second height 430. In some embodiments, first height 420 is greater than second height 430. First height 420 may depend on a desired attenuation rate or stopping power of incoming photons at PC sensor array 402. For example, as x-ray beam 406 enters a PC sensor of PC sensor array 402, a first portion of photons of x-ray beam 406 will be detected by the PC sensor, and a second portion of photons of x-ray beam 406 will pass through the PC sensor and be detected by an EID detector of EID detector array 404 positioned beneath the PC sensor. As the height of the PC sensor increases, a percentage of photons included in the first portion increases (e.g., more photons are detected in the PC sensor), and as the height of the PC sensor decreases, the percentage of photons detected in the first portion decreases. Therefore, the height of the PC sensors (e.g., first height 420) may be selected to achieve a desired attenuation rate or stopping power of PC sensor array 402.

The desired attenuation rate may be based on an expected pile-up behavior at PC sensor array 402. For example, as more photons are attenuated in PC sensor array 402, the expected pile-up behavior in each PC sensor of PC sensor array 402 increases. Thus, first height 420 may be selected to maintain the expected pile-up behavior below a desired threshold, above which the pile-up behavior may not be accurately corrected. Additionally, as semiconductor materials may have different attenuation rates, first height 420 may be selected based on a semiconductor material used in PC sensor array 402. For example, to achieve the desired attenuation rate, first height 420 may be greater if the semiconductor material is silicon, than if the semiconductor material is CZT or CdTe. The height of the EID detector may be selected to maximize DQE, to capture most of the x-rays (e.g., above 95%) that pass through PC sensors. For example, if a thickness of the PC detector is reduced to reduce pileup, a thickness of the EID detector may be increased to capture most of x-rays passed through.

An additional advantage of having smaller PC sensors than EID detectors is that some x-ray beams will enter PC sensor array 402 at boundaries between each PC sensor 414, where photons of the x-ray beams may not be detected by any PC sensor 414. For example, a boundary 440 between PC sensors of PC sensor array 402 is positioned directly above a boundary 442 between EID detectors of EID detector array 404, whereby an x-ray beam could pass undetected through both PC sensor array 402 via a boundary 440 and EID detector array 404 via a boundary 442. However, in contrast to an M=N configuration where the size of each PC sensor 414 is the same as the size of each EID detector 416 (e.g., where boundaries align), in the M>N arrangement shown in FIG. 4, photons of the x-ray beams entering PC sensor array 402 at some of the boundaries between each PC sensor 414 may be detected by an EID detector 416 positioned below the boundaries. For example, an x-ray beam passing through a boundary 444 between PC sensors of PC sensor array 402 may be detected by an underlying EID detector 416. As a result, a number of photons passing through both PC sensor array 402 and EID detector array 404 uncounted may be reduced, resulting in a higher DQE and so higher quality reconstructed image. Further, in some embodiments, an alignment of PC sensor array 402 and EID detector array 404 may be offset, such that the boundaries between each PC sensor 414 of PC sensor array 402 are not positioned directly above boundaries between each EID detector of EID detector array 404. In other words, by configuring the PC sensors in an overlapping fashion, the number of x-ray beams passing through both PC sensor array 402 and EID detector a 404 may be further reduced.

Additionally, if no signal is measured by PC sensor array 402 due to an x-ray beam passing through a boundary between PC sensors 414 (or due to a bad pixel), a corresponding measurement from the EID detector array 404 may be used to guide recovery of the missing data from PC sensor array 402. Similarly, if no signal is measured by EID detector array 404 due to an x-ray beam passing through a boundary between EID detectors 416, a corresponding measurement from a PC sensor 414 of PC sensor array 402 positioned above the boundary may be used to guide recovery of the missing data from EID detector array 404.

Referring now to FIG. 5A, a partial view of a multi-layer CT detector 500 of a PCCT system is shown. Multi-layer CT detector 500 may be a non-limiting embodiment of detector 308 of FIG. 3, where a plurality of rows of multi-layer CT detectors 500 may be arranged in a parallel configuration to form a detector array (e.g., detector array 108) for acquiring the projection data, as described above.

Multi-layer CT detector 500 includes a PC sensor array 502, an EID detector array 515, and a printed circuit board (PCB) 516. In the embodiment shown in FIG. 5A, PC sensor array 502, EID detector array 515, and PCB 516 are arranged vertically with respect to a direction of an incoming x-ray beam 501 (indicated by an arrow 507). EID detector array 515 is positioned below PC sensor array 502, and PCB 516 is positioned below EID detector array 515. In other embodiments, PC sensor array 502, EID detector array 515, and PCB 516 may be positioned relative to each other in a different configuration, as described in greater detail below.

When rows of multi-layer CT detectors 500 are arranged in the parallel configuration to form the detector array, rows of PC sensor arrays 502 and EID detector arrays 515 may form two-dimensional sensor arrays similar to PC sensor array 402 and EID detector array 404 described above in reference to FIG. 4.

PC sensor array 502 and EID detector array 515 may both be electronically coupled to an application-specific integrated circuit (ASIC) 512 mounted on PCB 516. As described in greater detail below, ASIC 512 may calculate photon counts detected at sensors of PC sensor array 502 and may digitize the integrated charge in EID detector array 515. PC sensor array 502 may be coupled to ASIC 512 via a plurality of wire bonds 514 that run within between-pixel reflector material in EID detector array 515, along a plurality of vias 513. EID detector array 515 may be electronically coupled to ASIC 512 via a plurality of wire bonds 519. Additionally, PCB 516 may include a connection 518 to readout electronics of the detector 500, which may also be used to calculate the number of photons detected PC sensor array 502 and to digitize the charge signal in EID detector array 515. The readout electronics may be external to PCB 516 (e.g., for use during assembly and testing). The readout electronics forms part of a DAS of the PCCT system (e.g., DAS 214).

PC sensor array 502 may be configured to count photons impacting edge 511 of PC sensor array 502. In various embodiments, PC sensor array 502 may be embedded in a chip made of a semi-conductor material, such as silicon. A width of the chip may be one pixel, at an edge 511 of PC sensor array 502. A plurality of sensors (e.g., such as sensor 414 of FIG. 4) may be embedded along a surface of the chip and extending along a length of the chip. Each sensor corresponds to a pixel 509 along edge 511. Each sensor may comprise one or more sensor segments 505, which may be embedded in a column 503 extending below each pixel 509, oriented in direction 507 of incoming x-ray beams 501 (e.g., vertically in FIG. 5A). Each sensor segment 505 of each column 503 may have a width across the surface of PC sensor array 502 of approximately one pixel, corresponding to pixel 509 at edge 511. Each sensor segment 505 of each column 503 may count a number of photons of an incoming x-ray beam 501 impacting edge 511 at pixel 509.

In other words, each column 503 may include a plurality of segments 505 stacked vertically in the column 503 in the direction 507. For example, each (vertically depicted) column 503 may include a first segment at a first vertical position 504; a second segment at a second vertical position 506, and so on. In the embodiment depicted in FIG. 5A, each column 503 includes two segments 505. In other embodiments, each column 503 may include two, three, four, or a different number of segments 505. A size of each segment 505 in a column 503 may be the same, or each segment 505 in a column 503 may be different. For example, a first segment 505 of a column 503 may be smaller than a second segment 505 of the column 503 to reduce pileup.

Each segment 505 may be electrically coupled to ASIC 512 mounted on PCB 516. In various embodiments, each segment 505 of PC sensor array 502 may be electrically coupled to a sensor bond pad 510 of PC sensor array 502 via a PCCT sensor trace 508. Sensor bond pad 510 may be electrically coupled to ASIC 512 via wire bond 514, which may pass through EID detector array 515 to PCB 516 along via 513.

Each segment 505 may detect a number of incoming photons in an x-ray beam 501. As the x-ray beam 501 impacts PC sensor array 502 at a pixel 509, the x-ray beam 501 may pass through a plurality of stacked segments 505 of a corresponding column 503. As the x-ray beam 501 passes through each stacked segment 505 of the column 503, a number of photons included in the x-ray beam 501 may be detected at the relevant segment 505.

For example, an exemplary x-ray beam 501 may enter a first segment 505 in the first vertical position 504 of the column 503, and the first segment 505 may detect a first number of photons of the exemplary x-ray beam 501. The first number of photons may be less than a total number of photons of the exemplary x-ray beam 501, where a second number of the total number of photons may pass through the first segment 505 undetected. The second number of (undetected) photons of the exemplary x-ray beam 501 passing through the first segment 505 may then enter a second segment 505 at the second vertical position 506 of the column 503. The second segment 505 may detect a third number of photons of the exemplary x-ray beam 501. The third number of photons may be less than the second number of photons, where a fourth number of photons may pass through the second segment 505 undetected, and so on.

The number of photons detected at each vertically stacked segment 505 of the column 503 may vary. A first portion of the photons in the exemplary x-ray beam 501 may be detected by the first segment 505; a second portion of the photons in exemplary x-ray beam 501 may be detected by the second segment 505; and so on for additional segments. For example, a large percentage of the photons in the exemplary x-ray beam 501 may be detected by the first segment 505, a smaller percentage of the photons in exemplary x-ray beam 501 may be detected at the second segment 505, and an even smaller percentage of the photons in exemplary x-ray beam 501 may be detected at a third segment 505. Further, some photons of the exemplary x-ray beam 501 may not be detected at any of the segments 505 of the column 503.

As x-ray beam 501 passes through PC sensor array 502, x-ray beam 501 may be attenuated to various degrees by the semiconductor material of PC sensor array 502. As photons are detected at first segment 505 and second segment 505, an amount of energy in x-ray beam 501 may decrease correspondingly. If not all of the photons in x-ray beam 501 are detected at first segment 505 and second segment 505 (nor any additional segments 505), the photons remaining in x-ray beam 501 may be detected at EID detector array 515 positioned underneath PC sensor array 502. Specifically, the energy remaining in x-ray beam 501 may be detected by an EID detector 530 of EID detector array 515 positioned below first segment 505 and second segment 505.

Each EID detector 530 may include a scintillator 532 that converts x-rays to light energy, and a photodiode 534 positioned below scintillator 532 that converts the light energy into an electrical signal. The electrical signal may be transmitted from a bond pad 521 of photodiode 534 to ASIC 512 via a wire bond 519. Each scintillator 532 of each EID detector 530 may be separated from one or more neighboring scintillators 532 of one or more neighboring EID detectors 530 by a cast reflector 536, which prevents light energy released in a corresponding scintillator 532 from bleeding into the one or more neighboring scintillators 532. While in FIG. 5A, EID detector 530 is depicted as having the same width as each segment 505 (e.g., one pixel), it should be appreciated that in other embodiments, the EID detectors 530 may be wider than the sensors of PC sensor array 502, as described above in reference to FIG. 4.

By positioning EID detector 530 underneath the segments 505, all of the photons of x-ray beam 501 may be detected by multi-layer CT detector 500. A first portion of the photons of x-ray beam 501 may be detected at PC sensor array 502, and a second portion of the photons of x-ray beam 501 may be detected at scintillator 532. Because EID detector 530 is positioned underneath first segment 505 and second segment 505, a height of PC sensor array 502 (e.g., and/or heights of first segment 505, and second segment 505) may be configured such that a desired amount of x-ray flux is detected as photons by PC sensor array 502, where the desired amount of x-ray flux is a number of photons that can accurately be corrected for pile-up behavior. Thus, the height of PC sensor array 502 may be reduced without impacting the quality of the resulting reconstructed image, which may reduce a cost of multi-layer CT detector 500 due to less semiconductor material being needed. For example, if the semiconductor material is silicon, a smaller and less expensive chip may be used.

When a photon hits a segment 505, an analog electrical signal is generated that is transmitted to ASIC 512 via sensor trace 508 and sensor bond pad 510, where the analog electrical signal is proportional to an amount of energy of the photon. ASIC 512 may convert the analog electrical signal to a digital signal by counting the occurrence of the photon hit in a counter. Furthermore, the ASIC may discern the energy deposited by the photon by comparing the amount of electrical signal to one or more pre-established thresholds. Specifically, ASIC 512 may include a plurality of comparators, where each comparator of the plurality of comparators outputs a trigger signal that causes a corresponding digital counter to increment by one when the analog signal exceeds a signal level threshold associated with the comparator. Each comparator of the plurality of comparators may have a different signal level threshold. For example, ASIC 512 may include a first comparator with a first signal level threshold; a second comparator with a second signal level threshold, the second signal level threshold higher than the first signal level threshold; a third comparator with a third signal level threshold, the third signal level threshold higher than the second signal level threshold; and so on, up to a maximum energy level of a spectrum of photons. The differences between pairs of thresholds define energy ranges or bins. Thus, the number of photons whose energies fall within each bin may be recorded by the ASIC (or the readout electronics). These numbers of photon counts may be transmitted by the ASIC to the PCB via connection 524 to be used for image reconstruction. Alternatively, the ASIC may first perform additional operations on the numerical count information, such as summing together the individual photon counts from the bins within a given column to produce a total number of photon counts.

An advantage of including a plurality of segments in each column 503 is that pile-up behavior may be more accurately accounted for. X-rays are absorbed throughout a depth of the semi-conductor material (e.g., silicon), without regard for how it is divided up into segments. Each segment 505 acts as an independent sensing element capable of producing signals from an x-ray that is absorbed in it. As a result, each segment 505 counts x-rays that are absorbed within an area of the semi-conductor material associated with the segment 505, while other x-rays may not be absorbed and pass through the segment 505. Since each segment 505 is connected to its own counting channel circuit in the ASIC, the total number of x-ray counts are spread across multiple channels. Each channel can thereby more easily keep up with an absorption rate.

While dividing each sensor of PC sensor array 502 into segments may reduce the effects of photon pile-up, pile-up may still occur and may still lead to inaccuracies in photon counts. However, advantageously positioning EID detector array 515 below PC sensor array 502 may allow a size of PC sensor array 502 and a size of EID detector a 515 to be selected to maximize an efficiency of a pile-up correction, and to maximize a quality of images reconstructed using PC sensor data and EID detector data. An advantage of the multi-layer CT detector 500 is that all electronics are beneath both detectors, limiting signal loss and allowing for small detector elements that can be arrayed to make large detectors, which may enable a more compact design than routing large detector elements a different location (e.g., a side of the CT detector).

Also, by advantageously positioning EID detector array 515 below PC sensor array 502, the pile-up correction applied to a photon count of a PC sensor may be guided by data from an EID detector positioned underneath the PC sensor. Specifically, an incident flux detected at the EID detector positioned underneath the PC sensor may be used to adjust the pile-up correction. The response of the EID detector is linear to the total energy of detected x-rays. Since the spectrum of x-rays varies after passing through patients and PC detector, both PC and EID may be used during the pileup calibration. At low x-ray flux, both PC and EID data will show linear response to the incoming x-rays. PC data may be linear for all energy bins (energy spectrum). At high x-ray flux, PC data may deviate from the linear response due to pileup while EID data maintain its linearity. Both the energy spectrum of PC data and EID incident flux rate data may be used to calculate pileup calibration vectors using a pileup model formula. Since the EID data is linear independent of x-ray flux, it improves the quality of the pileup calibration. The pileup calibration vectors will be applied to patient data for pileup correction.

FIG. 5B. shows a side perspective view 550 of multi-layer CT detector 500 of FIG. 5A. In the side perspective view 550, a plurality of PC sensor arrays are shown arranged above a two-dimensional EID detector array 551. Each PC sensor array of the plurality of PC sensor arrays may be a non-limiting example of PC sensor array 502 of FIG. 5A, and EID detector array 551 may be a non-limiting example of EID detector array 515 of FIG. 5A. The plurality of PC sensor arrays includes a first PC sensor array 552, a second PC sensor array 554, a third PC sensor array 556, and a fourth PC sensor array 558. EID detector array 515 includes a plurality of EID detectors, such as a first EID detector 560 and a second EID detector 562. First EID detector 560 may be separated from the second EID detector 562 by a cast reflector 564 (e.g., cast reflector 536 of FIG. 5A). It should be appreciated that the side perspective view 550 may include a portion of multi-layer CT detector 500, where additional PC sensor arrays and/or EID detectors may be included without departing from the scope of this disclosure.

FIG. 5B shows relative thicknesses of different components of multi-layer CT detector 500. In FIG. 5B, each EID detector of the plurality of EID detectors may have a length, width, and/or thickness that is different from each PC sensor array of the plurality of PC sensor arrays. For example, a thickness 570 of first PC sensor array 552, second PC sensor array 554, third PC sensor array 556, and fourth PC sensor array 558 may be less than a thickness 572 of first EID detector 560 and second EID detector 562. As a result of thickness 570 being less than thickness 572, a plurality of PC sensor arrays may be aligned with a different plurality of EID detectors of EID detector array 551. For example, first PC sensor array 552 and second PC sensor array 554 may be positioned above first EID detector 560, and third PC sensor array 556 and fourth PC sensor array 558 may be positioned above second EID detector 562. As a result, an incoming x-ray beam 580 entering a PC sensor of first PC sensor array 552 may be partially attenuated within the first PC sensor array 552, where a weakened x-ray beam 580 (e.g., with less energy) may pass through first PC sensor array 552 to be detected at first EID detector 560. Similarly, an incoming x-ray beam 582 entering a PC sensor of second PC sensor array 554 may be partially attenuated within the second PC sensor array 554, where a weakened x-ray beam 582 may pass through second PC sensor array 554 to also be detected at first EID detector 560. In contrast, an incoming x-ray beam 584 entering a PC sensor of third PC sensor array 556 may be partially attenuated within third PC sensor array 552, where a weakened x-ray beam 584 may pass through third PC sensor array 556 to be detected at second EID detector 562, and an incoming x-ray beam 586 entering a PC sensor of fourth PC sensor array 558 may be partially attenuated within fourth PC sensor array 558, where a weakened x-ray beam 586 may pass through fourth PC sensor array 558 to be detected at second EID detector 562.

In the depicted embodiment, each of first PC sensor array 552, second PC sensor array 554, third PC sensor array 556, and fourth PC sensor array 558 is electrically coupled to ASIC 512 via a respective wire bond 522 (e.g., and via wire bonds channeled through pathways or vias in cast reflector 564). Each of first EID detector 560 and second EID detector 562 is also electronically coupled to ASIC 512, via a respective wire bond 519. In other embodiments, one or more additional ASICs 512 may be mounted on PCB 516, where a portion of PC sensor arrays and/or a portion of the EID detector arrays may be electronically coupled to the one or more additional ASICs 512.

One advantage of this configuration is that x-rays that fall between PC sensors or PC sensor arrays may be detected at an EID detector positioned below the PC sensor array. For example, an x-ray beam 590 may enter multi-layer CT detector 500 between first PC sensor array 552 and second sensor array 554, where x-ray beam 590 may not be detected at either first PC sensor array 552 or second sensor array 554. However, x-ray beam 590 may enter into and be detected by EID detector 560 positioned underneath first PC sensor array 552 and second sensor array 554. Thus, because EID detectors 560 and 562 partially overlap PC sensor arrays 552, 554, 556, and 558, x-ray beams passing through the PC sensor layer of multi-layer CT detector 500 undetected may be detected at the EID detector array of multi-layer CT detector 500, resulting in a higher quality reconstructed image.

A second advantage of the configuration of FIGS. 5A and 5B is that by positioning the electronics (e.g., PCB 516, ASIC 512, etc.) underneath the EID detector array, a length of the circuits and electronic connections between the PC sensor arrays, the EID detectors, and other elements may be reduced, resulting in less signal loss than in other configurations, as well as a smaller size CT detector with a reduced cost of materials. Positioning the electronics underneath the EID detector array may allow for smaller detector elements that can be advantageously arrayed to create larger detectors in a cost-efficient manner.

FIGS. 5A and 5B show various advantages of a CT detector including an EID detector array positioned below a PC sensor array, where electronics including PCB 516, ASIC 512, and other readout electronics are configured below the EID detector array and PC sensor array in a vertical configuration. In contrast, FIGS. 6A, 6B, 6C, 6D, and 6E show alternative configurations of a multi-layer CT detector including an EID detector array positioned below a PC sensor array, where a portion of the electronics are not arranged underneath the EID detector array.

FIG. 6A shows an alternative configuration 600 of a PC sensor array included in the CT detector, where electronics including an ASIC used to count photons and measure energy in incoming x-ray beams are positioned to one side of the sensor array. In alternative configuration 600, a PC sensor array 606 is formed by attaching a silicon chip 602 to a flexible or ceramic PCB 604, upon which an ASIC 616 is mounted to one side of silicon chip 602. Silicon chip 602 may be divided into a plurality of PC sensors 610, where each PC sensor 610 may include one or more sensor segments, as described above in reference to FIG. 5A. Each PC sensor 610 may include a solder point 612, by which the PC sensor 610 may be bonded to a corresponding circuit 614 embedded in PCB 604 that electronically connects the PC sensor 610 to ASIC 616. A perspective view 608 shows a top of PC sensor array 606, where silicon chip 602 at a front side 622 of PC sensor array 606 is attached to PCB 604 at a back side 620 of PC sensor array 606. In contrast to the CT detector shown in FIGS. 5A and 5B, ASIC 616 is shown positioned at one side of PC sensor array 606, rather than below PC sensor array 606 (e.g., underneath an EID detector array).

FIG. 6B shows a first perspective view 650 of a CT detector including a plurality of PC sensor arrays, where each PC sensor array of the plurality of PC sensor arrays may be a non-limiting example of PC sensor array 606 of FIG. 6A. The plurality of PC sensor arrays includes a first PC sensor array 651, a second PC sensor array 652, a third PC sensor array 653, a fourth PC sensor array 654, a fifth PC sensor array 655, and a sixth PC sensor array 656, arranged in a parallel configuration to create a two-dimensional array of individual PC sensors, as described above in reference to FIG. 4. First perspective view 650 shows an alignment of the plurality of PC sensor arrays with a plurality of EID detectors of an EID detector array 659, where first PC sensor array 651, second PC sensor array 652, and third PC sensor array 653 may be positioned above EID detectors of a first EID detector row 657, and fourth PC sensor 654, fifth PC sensor 655, and sixth PC sensor 656 may be positioned above EID detectors of a second EID detector row 658. Thus, a first portion 660 of PC sensors (e.g., PC sensors 610) included in first PC sensor array 651 may be positioned above a first EID detector 663 of first EID detector row 657; a second portion 661 of PC sensors included in first PC sensor array 651 may be positioned above a second EID detector 664 of first EID detector row 657; and a third portion 662 of PC sensors included in first PC sensor array 651 may be positioned above a third EID detector 665 of first EID detector row 657. Similarly, a first portion 660 of PC sensors included in second PC sensor array 652 and third PC sensor array 653 may be positioned above first EID detector 663; a second portion 661 of PC sensors included in second PC sensor array 652 and third PC sensor array 653 may be positioned above second EID detector 664; and a third portion 662 of PC sensors included in second PC sensor array 652 and third PC sensor array 653 may be positioned above third EID detector 665.

FIG. 6C shows a second perspective view 670 of the CT detector of FIG. 6B, where second perspective view 670 shows a side view of an alignment of EID detectors underneath PC sensor arrays, with respect to a descending x-ray beam 601. FIG. 6C shows a PC sensor array 606 (such as PC sensor arrays 651, 652, 653, 654, 655, and 656), which is positioned above a first EID detector 672, a second EID detector 673, and a third EID detector 674 of an EID detector array 677. For example, first EID detector 672 may correspond to EID detector 663 of FIG. 6B; second EID detector 673 may correspond to EID detector 664; and third EID detector 674 may correspond to EID detector 665. A photodiode layer 675 of the CT detector may include a plurality of photodiodes (e.g., photodiode 534 of FIG. 5A), which convert photons detected at first EID detector 672, second EID detector 673, and third EID detector 674 to electrical signals that may be routed to a second ASIC 676 of the CT detector.

For example, an x-ray beam 601 may enter a PC sensor 671 of PC sensor array 606. A portion of a total number of photons of x-ray beam 601 may be detected at PC sensor 671. The detected portion of photons may be counted at ASIC 616. As a result of not all of the photons of x-ray beam 601 being detected, x-ray beam 601 may pass through PC sensor 671 and enter EID detector 672. However, as a result of the portion of photons being detected at PC sensor 671, a portion of x-ray beam flux 601 entering EID detector 672 may be reduced. EID detector 672 may convert the energy of x-ray beam 601 into light, which may generate a current at a photodiode of photodiode layer 675. The current may be routed to second ASIC 676 of the CT detector, which may be positioned underneath photodiode layer 675. The reduced flux of x-ray beam 601 detected by the photodiode and a photon count of the portion of photons detected at PC sensor 671 may then both be used to reconstruct an image.

By reconstructing the image based on both data from PC sensor 671 and EID detector 672, a resolution of the image may be as high as an image reconstructed by a PCCT detector (e.g., higher than may be achieved by an EID detector alone), and a noise level of the image may be lower than a noise level of the image reconstructed by a PCCT detector. The higher resolution may be a result of PC sensor 671 being smaller than a PC sensor of a PCCT detector without an EID detector layer, and data from EID detector 672 being used to guide a pile-up correction applied to a photon count from PC sensor 671, among other factors described herein.

For spectral information estimation, multiple energy bin PC data from PC sensor 671 may be used. However, EID data from EID detector 672 may also be used. The EID data may be treated as an independent wide bin response. Through system response modelling and/or phantom calibration, the EID data as well as the PC data may be used as part of a material decomposition process.

Further, the EID data itself may be used to generate conventional kVp images without the PC data. This may be clinically advantageous when fast throughput is desired and conventional CT images are desired. Since EID projections are filtered by the PC sensors, a narrower energy spectrum may be expected, resulting in an improved beam-hardening performance when images are reconstructed from EID projections alone. To reduce noise in an image generated from the EID data, a photon count from a PC sensor may be combined with the EID data to generate the conventional kVp images. Combining the photon count from the PC sensor with the EID data may include assigning energy weightings to the PC sensor data and the EID data.

FIG. 6D shows an alternative configuration 680 of the CT detector of FIG. 6C, where a PC sensor array 681 includes a plurality of silicon chips 602 attached to a single PCB 688 including ASIC 616 positioned at a side of PC sensor array 681. For example, PC sensor array 681 includes a first silicon chip 682 including a plurality of sensors 610; a second silicon chip 684 including a plurality of sensors 610; and a third silicon chip 686 including a plurality of sensors 610, where each of the sensors 610 of first silicon chip 682, second silicon chip 684, and third silicon chip 686 are electronically coupled to ASIC 616. In some embodiments, one or more additional ASICs 616 may be included on PCB 688. Each of the sensors 610 of first silicon chip 682, second silicon chip 684, and third silicon chip 686 may be positioned above an EID detector of an EID detector array 689, as described above.

FIG. 6E shows a CT detector 690 in a similar configuration as shown in FIG. 6C, but where a different semiconductor material (e.g., other than silicon) is used in a PC sensor array 691. For example, the different semiconductor material may be Cadmium Zinc Telluride (CZT), or Cadmium Telluride (CdTe), or a different type of semiconductor material. Like PC sensor array 606 of FIG. 6A, PC sensor array 691 includes a plurality of PC sensors (e.g., sensor segments) 694, each PC sensor 694 electronically coupled to an ASIC 696 configured to count photons detected at the plurality of PC sensors 694. A density of the different semiconductor material may be greater than a density of silicon, where each PC sensor 694 may have a height (with respect to a descending x-ray beam 601) that is shorter (e.g., 1-3 mm) than a height of silicon chip 602 (e.g., 10-50 mm).

Unlike FIGS. 6A-6D, ASIC 696 is positioned underneath an EID detector array 697 (e.g., EID detector array 677), which includes a plurality of EID detectors 698 arranged above a photodiode layer 699, as described above. PC sensor array 691 may be electronically coupled to ASIC 696 via one or more flexible cables 693, which may allow ASIC 696 to be positioned below photodiode layer 699. By positioning ASIC 696 below EID detector array 697, an amount of material between PC sensor array 691 and EID detector array 697 may be minimized. Since any material between PC sensor array 691 and EID detector array 697 absorbs x-rays, an efficiency of CT detector 690 may be increased by minimizing the amount of material between PC sensor array 691 and EID detector array 697, resulting in reconstructed images of a higher quality. A second ASIC 695 may be positioned underneath photodiode layer 699, which may be used to determine an amount of energy detected in x-ray beams passing through PC sensor array 691 and entering an EID detector 698 of EID detector array 697. Thus, each image reconstructed based on x-rays detected by CT detector 690 may be reconstructed using photon counts detected at PC sensor array 691 and counted at ASIC 696, and x-ray beam energies measured at EID detector array 697 and integrated at ASIC 695.

Figure 7:
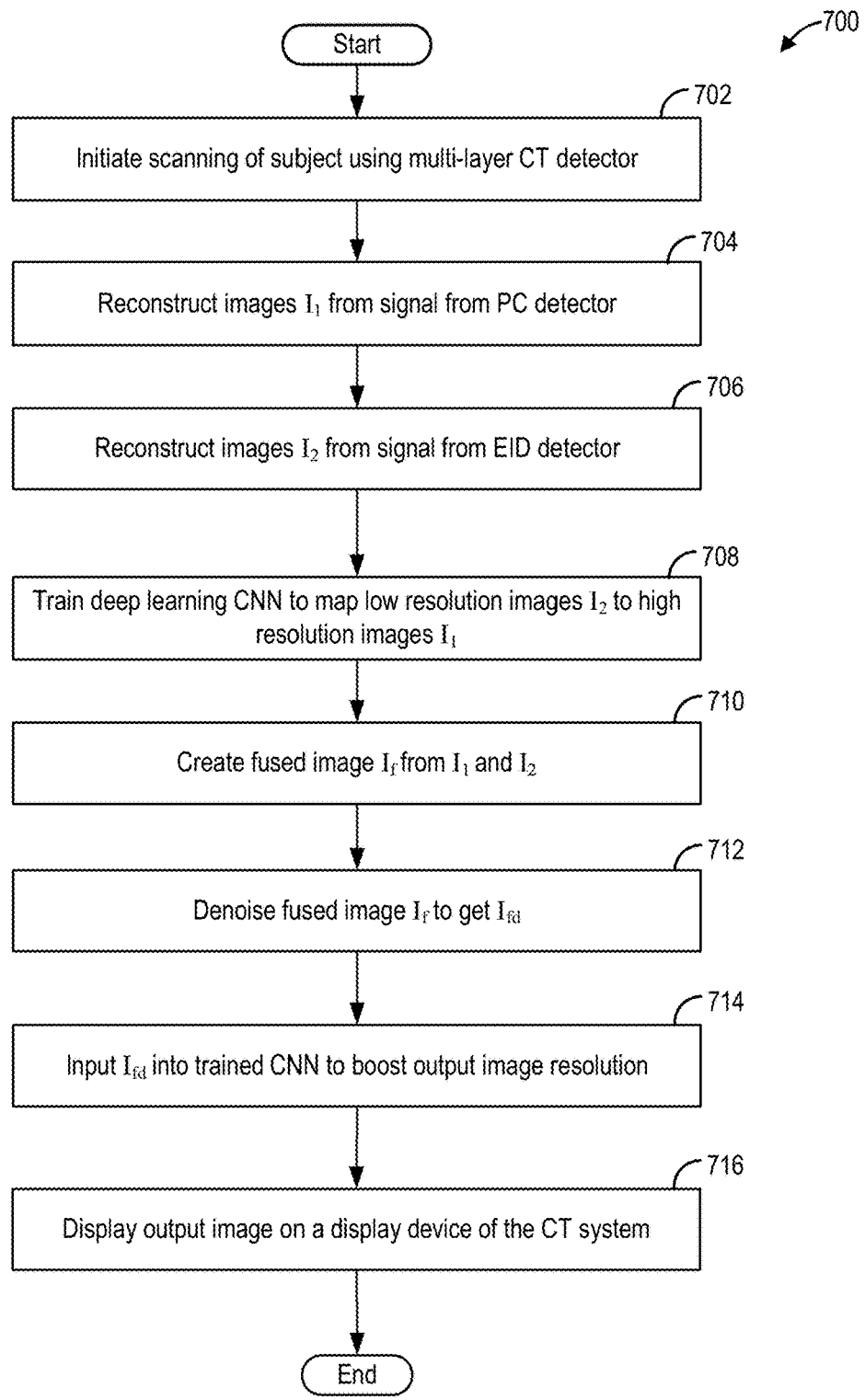
FIG. 7 is a flowchart illustrating an exemplary method for increasing a resolution of images reconstructed from PC data and EID data, in accordance with one or more embodiments of the present disclosure.

Referring now to FIG. 7, a flowchart is shown illustrating an exemplary method 700 for increasing a resolution of images reconstructed from x-rays entering a multi-layer CT detector (e.g., multi-layer CT detector 500) of a CT system, using PC data received from PC sensors of a PC sensor array (e.g., PC sensor array 402) of the multi-layer CT detector and EID data received from EID detectors of an EID detector array (e.g., EID detector array 404) of the multi-layer CT detector. As described above, by reconstructing images based on both the PC data and the EID data, a greater number of photons of the x-rays may be detected, and the EID data may be used to guide a pile-up correction of the PC data, resulting in images of a higher resolution and with a lower amount of noise than images reconstructed from PC sensors or EID detectors alone. In addition, method 700 may be used to further increase the resolution, using a trained convolutional neural network as described below. Method 700 may be stored as instructions in a non-transitory memory and executed by one or more processors of a computing device of a CT imaging system, such as computing device 216 of imaging system 200 of FIG. 2.

Method 700 begins at 702, where method 700 includes initiating scanning of a subject using a multi-layer CT detector. The multi-layer CT detector may include a first layer of PC sensors superimposed above a second layer of EID detectors, as described above in reference to FIG. 4. In some embodiments, the multi-layer CT detector may be a non-limiting example of multi-layer CT detector 500 of FIGS. 5A and 5B, or multi-layer CT detector 690 of FIG. 6E, where readout electronics of the multi-layer CT detector are arranged underneath the second layer of EID detectors with respect to a direction of an incoming x-ray. In other embodiments, the multi-layer CT detector may be a non-limiting example of the multi-layer CT detector described in reference to FIGS. 6A-6D, where a first readout electronics configured to count photons at each PC sensor array of the first layer of PC sensors is positioned to one side of the PC sensor array, and a second readout electronics configured to measure an energy of x-ray beams entering EID detectors of the second layer of EID detectors is positioned underneath the second layer of EID detectors.

At 704, method 700 includes reconstructing a first set of images $I_1$ based on signals received from the first layer of PC sensors of the multi-layer CT detector after the PC data gets pileup corrected using both PC and EID data. The signals may be transmitted from a plurality of PC sensor arrays of the first layer of PC sensors, such as PC sensor arrays 606 of FIG. 6A, to corresponding readout electronics such as an ASIC (e.g., ASIC 512 or ASIC 616).

At 706, method 700 includes reconstructing a second set of images $I_2$ based on signals received concurrently from the second layer of EID detectors of the multi-layer CT detector (e.g., where the images are generated from the same set of x-ray beams). The signals may be transmitted from a plurality of EID detectors of the second layer of EID detectors, such as EID detectors 663, 664, and 665 of FIG. 6B, to readout electronics corresponding to the EID detectors (e.g., ASIC 512 or ASIC 676 of FIG. 6C). The images $I_2$ may have a resolution that is lower than the images $I_1$, as a result of a first size of the PC sensors being smaller than a second size of the EID detectors. Both $I_1$ and $I_2$ may be noisy, because both use part of the incident x-ray signal.

At 708, method 700 includes training a deep learning CNN to map the lower resolution images $I_2$ to the higher resolution images $I_1$. Prior to training the deep learning CNN, input image pairs ($I_2$, $I_1$) are generated, where the images $I_2$ are input images, and the images $I_1$ are ground truth images. During training of the CNN, for each input image $I_2$ inputted into the CNN, weights at various layers of the CNN are adjusted via a gradient descent process using backpropagation to minimize a calculated difference between an output of the CNN the corresponding ground truth image $I_1$ of the relevant image pair. After training the CNN, when a new reconstructed image is inputted into the trained CNN, the trained CNN may output a higher-resolution version of the new reconstructed image.

At 710, method 700 includes creating a fused image $I_f$ from each image pair ($I_2$, $I_1$). In various embodiments, the fused image $I_f$ may be a weighted combination of the images $I_1$ and $I_2$, where $I_f=aI_1+bI_2$. The parameters a and b may be adjusted to minimize an amount of noise in $I_f$, or to maximize a resolution of $I_f$, or to achieve a target resolution and a target noise level. Following this fusion step, the fused image $I_f$ may have a lower amount of noise than both $I_1$ and $I_2$, and a resolution that is higher than $I_2$ but lower than $I_1$. The target noise level can be achieved by commonly used methods. For example, a water phantom may be scanned and image $I_1$ and $I_2$ reconstructed. Because the water phantom image is uniform, the noise level on $I_1$ and $I_2$ and fusion image $I_f=aI_1+bI_2$ can be measured. In order to minimize output image noise level or get a curtain noise level, search for proper value for a and b, the output fusion image $I_f=aI_1+bI_2$ will have minimal noise or curtain level noise. In order to get a specified resolution which is between the resolution of image $I_1$ and $I_2$, a resolution phantom with tungsten wire may be scanned, and image $I_1$ and $I_2$ reconstructed, and the resolution for the fusion image $I_f$ can be measured for a given a and b. By searching proper value for a and b, a target resolution for $I_f$ can be achieved.

At 712, method 700 includes denoising the fused image $I_f$ to generate a denoised fused image $I_{fd}$. The fused image $I_f$ may be denoised with a conventional weighted average method, or guided noise reduction or deep learning noise reduction to generate the denoised image $I_{fd}$. In the weighted average denoising method, the output value for pixel (i,j) is computed with the following equation, where w is the weight for a pixel in the neighborhood and N is used to define the neighborhood size. Normally, the w is calculated from $I_f$ for weighted average methods. The weights can be calculated using various methods, for example, bilateral filtering or non-local means methods.

$$I_{fd}(i, j) = \frac{\sum_{a,b=-N}^{N} I_f(i+a, j+b) * w(i+a, i+b)}{\sum_{a,b=-N}^{N} w(i+a, i+b)}$$

In guided denoising, the weights may be calculated from a guide image. For example, the $I_2$ image can be used as guide image because it has lower noise than $I_1$ and $I_f$. The weights may be calculated from $I_2$ using various methods, for example, bilateral filtering or non-local means methods. Deep learning denoising may also be used. A set of CT image patches with low noise or no noise may be prepared as ground truth images, and a set of CT noise patches may be prepared. The ground truth CT image patches and CT noise patches are used as input for the deep learning neural network. The corresponding ground truth images may be used as output of the deep learning neural network. During the training process, the neural network may optimize the network weights to minimize a difference between a network output image and the ground truth image patches. When the network is trained, a set of network weights are acquired. In the denoising process, a CT image from a scan is inputted into the network to generate the denoised CT output image.

At 714, method 700 includes inputting the denoised, fused image $I_{fd}$ into the trained deep learning CNN to generate an inference output image $I_{output}$ with a higher resolution than the denoised, fused image $I_{fd}$. Because $I_{fd}$ has a decreased amount of noise as a result of step 712, the noise will not be increased too much by the trained CNN during the inference stage. As a result of feeding the denoised, fused image $I_{fd}$ into the trained deep learning CNN, the resulting output image $I_{output}$ may have a resolution that is as high as could be obtained with a photon counting CT system, but with lower noise.

At 716, method 700 includes displaying the output image on a display device of the CT system, and method 700 ends.

In another embodiment, each image $I_2$ and $I_1$ of the image pairs ($I_2$, $I_1$) may be denoised prior to training the deep learning CNN (e.g., via the conventional weighted average method, guided noise reduction, or deep learning noise reduction of step 712). The CNN may then be trained on a set of denoised image pairs ($I_{2d}$, $I_{1d}$), where the images $I_{2d}$ are input images, and the images $I_{1d}$ are ground truth images. A result of training the CNN on the denoised image pairs ($I_{2d}$, $I_{1d}$), as opposed to the original image pairs ($I_2$, $I_1$), is that during a subsequent inference stage (e.g., with new reconstructed images based on the PC data and the EID data), the trained CNN may output images with an increased resolution and a smaller increase in noise. The images outputted by the trained CNN may then be fused as described at step 710, where the parameters a and b may be adjusted to further increase the resolution and decrease the noise of the resulting fused image.

Thus, the multi-layer CT detector configuration including a first PC sensor layer and a second EID detector layer provides a new approach to reconstructing images from CT scan data that leverages advantages of both PC and EID detectors to achieve higher image quality for various clinical CT applications, including spectral and non-spectral tasks. By combining the two technologies, various challenges to generating high quality reconstructed images may be overcome. Data sizes may be reduced and thermal and power management may be improved by positioning the second EID detector layer underneath the first PC sensor layer, and by positioning readout electronics underneath the second EID detector layer. Including the second EID detector layer underneath the first PC sensor layer may allow a height of PC sensors in the PC sensor layer to be reduced, which may reduce a size and cost of silicon chips used in the PC sensor layer. In some embodiments, costs of the multi-layer CT detector may be further reduced by positioning a first readout electronics (e.g., for photon counting sensors) to a side of PC sensor arrays, and positioning a second readout electronics (e.g., for EID data) underneath the EID detector layer.

Because the second EID detector layer can detect an energy level of incident x-rays passing through the PC sensor layer, the PC sensor layer may include PC sensors of a smaller size than the EID detectors, thereby increasing a resolution of resulting images. EID data may also be used to increase an accuracy of a pile-up correction applied to PC sensor data, resulting in increased resolution and lower noise. An additional advantage of having EID detectors that are larger than the PC sensors is that x-rays that pass through gaps between boundaries of adjacent PC sensors may be detected by underlying EID detectors, increasing a number of x-rays and an amount of overall photons detected by the multi-layer CT detector. If fast throughput is desired, the EID detector data may be used to reconstruct images without using the PC sensor data, where the EID detector data may be more accurate than a single-layer EID detector due to a filtering effect of the PC sensor layer that may harden the x-ray beams.

As a result of the various advantages of the multi-layer CT detector, images may be reconstructed with a resolution greater than an EID detector and similar to a PCCT detector, with less noise than the PCCT detector. Additionally, a method is provided for further increasing a resolution of images generated by the PC sensor data and the EID detector data without increasing an amount of noise, using a CNN trained using image pairs including an input image from the EID detector data and a target image from the PC sensor data. With both PC and EID detectors in one system and measuring the same object at the same time, better corrections can be made in the image chain, generating images with high spatial resolution and lower noise, and offering more opportunities for advanced clinical applications while supporting the routine clinical needs for a CT system.

The technical effect of a multi-layer CT detector including a first layer of PC sensors and a second layer of EID detectors arranged underneath the PC sensors is that images may be reconstructed with a resolution greater than an EID detector and similar to a PCCT detector, with less noise than the PCCT detector.

The disclosure also provides support for a computed tomography (CT) detector system, comprising: a layer of energy integrating detectors (EID) arranged at an opposite side of a layer of photon counting (PC) sensors with respect to an incoming x-ray, where a number of the PC sensors exceeds a number of the EID detectors. In a first example of the system, the system further comprises: an image processing unit configured to correct PC data using EID data, and denoise and increase a resolution of an image reconstructed from EID data and PC data using a deep learning convolutional neural network (CNN) trained on pairs of images, each pair of images including a target image reconstructed from a first signal from the layer of PC sensors, and an input image reconstructed from a second signal from the layer of EID detectors, the EID data and PC data acquired concurrently from a same patient ray path. In a second example of the system, optionally including the first example, the PC data and the EID data are both used to generate spectral information and non-spectral information. In a third example of the system, optionally including one or both of the first and second examples, the image is reconstructed from the EID data and not from the PC data. In a fourth example of the system, optionally including one or more or each of the first through third examples, boundaries between each PC sensor of the number of PC sensors are not aligned with boundaries between each EID detector of the number of EID detectors. In a fifth example of the system, optionally including one or more or each of the first through fourth examples, the system further comprises: readout electronics positioned at an opposite side of the layer of EID detectors as an incoming x-ray, wherein signals from each PC sensor of the number of PC sensors are transmitted to the readout electronics via wire bonds that are routed between the EID detectors. In a sixth example of the system, optionally including one or more or each of the first through fifth examples, the system further comprises: a first set of readout electronics and a second set of readout electronics, wherein signals from each EID detector of the number of EID detectors are transmitted to the first set of readout electronics, and signals from each PC sensor of the number of PC sensors are transmitted to the second set of readout electronics. In a seventh example of the system, optionally including one or more or each of the first through sixth examples, the first set of readout electronics and the second set of readout electronics are positioned at the opposite side of the layer of EID detectors as an incoming x-ray, and signals from each PC sensor of the number of PC sensors are transmitted to the second set of readout electronics via one or more flexible cables routed around the layer of EID detectors. In an eighth example of the system, optionally including one or more or each of the first through seventh examples, the first set of readout electronics is positioned at the opposite side of the layer of EID detectors as an incoming x-ray, and the second set of readout electronics is positioned to one side of the layer of PC sensors. In a ninth example of the system, optionally including one or more or each of the first through eighth examples, the PC sensors of the layer of PC sensors are arranged in two-dimensional PC sensor arrays, each PC sensor array including a semiconductor material attached to a printed circuit board (PCB) including a readout electronics of the second set of readout electronics and a plurality of circuits, each circuit of the plurality of circuits electronically coupling a PC sensor of the PC sensor array to the readout electronics. In a tenth example of the system, optionally including one or more or each of the first through ninth examples, the image processing unit is configured to correct PC data using EID data by adjusting a pile-up correction applied to a photon count detected at a PC sensor of the layer of PC sensors based on both PC data energy spectrum and an incident flux rate detected at an EID detector positioned at an opposite side of the layer of PC sensors as an incoming x-ray. In a eleventh example of the system, optionally including one or more or each of the first through tenth examples, increasing the resolution of the image reconstructed from EID data and PC data using the deep learning CNN trained on pairs of images including a target image reconstructed from a first signal from the layer of PC sensors, and an input image reconstructed from a second signal from the layer of EID detectors further comprises: creating a fused image from the target image and the input image, denoising the fused image using at least one of a weighted average method, a guided noise reduction, and a deep learning noise reduction, inputting the denoised, fused image into the trained CNN to generate an output image, the output image having a higher resolution than the denoised, fused image.

The disclosure also provides support for a method for a computed tomography (CT) system, the method comprising: reconstructing a first image based on photon counting (PC) data received from a PC sensor layer of a CT detector of the CT system, reconstructing a second image based on energy integration (EI) data received from an EID detector array of the CT detector, training a convolutional neural network (CNN) to increase a resolution of the second image, using the first image as ground truth data, combining the first image and the second image to generate a fused image, inputting the fused image into the trained CNN to generate an output image, the output image having a higher resolution and a lower noise than the fused image, and displaying the output image on a display device of the CT system. In a first example of the method, the EID detector array is positioned at an opposite side of the PC sensor layer as an incoming x-ray. In a second example of the method, optionally including the first example, boundaries between PC sensors of the PC sensor layer are not aligned with boundaries between EID detectors of the EID detector array. In a third example of the method, optionally including one or both of the first and second examples, combining the first image and the second image to generate the fused image further comprises weighting the first image by a first parameter and weighting the second image by a second parameter. In a fourth example of the method, optionally including one or more or each of the first through third examples, the first parameter and the second parameter are selected to perform one of minimizing an amount of noise in the fused image and maximizing a resolution of the fused image. In a fifth example of the method, optionally including one or more or each of the first through fourth examples, the method further comprises: denoising the fused image using at least one of a weighted average method, a guided noise reduction, and a deep learning noise reduction. In a sixth example of the method, optionally including one or more or each of the first through fifth examples, reconstructing the first image based on the PC data received from the PC sensor layer further comprises performing a pile-up correction on photon counts of the PC data, the pile-up correction based on the EID data received from the EID detector array.

The disclosure also provides support for a computed tomography (CT) detector, comprising: a first number of photon counting (PC) sensors arranged in a first layer of the CT detector, a second number of energy integrating detectors (EID) arranged in a second layer of the detector, the second layer on an opposite side of the first layer with respect to an incoming x-ray, the second number less than the first number, and one or more readout electronics electronically coupled to the first number of PC sensors and the second number of EID detectors, the one or more readout electronics arranged on an opposite side of the second layer with respect to the incoming x-ray, the one or more readout electronics receiving signals from the first number of PC sensors via a plurality of circuits routed along pathways through cast reflectors of the second number of EID detectors or around the second number of EID detectors via a flexible cable.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A computed tomography (CT) detector system, comprising:
a layer of energy integrating detectors (EID) arranged at an opposite side of a layer of photon counting (PC) sensors with respect to an incoming x-ray, where a number of the PC sensors exceeds a number of the EID detectors; and
an image processing unit configured to:
train a deep learning convolutional network (CNN) on pairs of images, each pair of images including a target image reconstructed from a first signal from the layer of PC sensors and an input image reconstructed from a second signal from the layer EID detectors;
for one or more of the pairs of images, generate a fused image from the target image and the input image, wherein to generate the fused image, the image processing unit is configured to weight the target image by a first parameter and weight the input image by a second parameter; and
generate an output image with the trained deep learning CNN based on the fused image, wherein the output image has a higher resolution than the fused image.

2. The CT detector system of claim 1, wherein the EID data and PC data acquired concurrently from a same patient ray path.

3. The CT detector system of claim 1, wherein the PC data and the EID data are both used to generate spectral information and non-spectral information.

4. The CT detector system of claim 1, wherein the image is reconstructed from the EID data and not from the PC data.

5. The CT detector system of claim 2, wherein the image processing unit is configured to correct PC data using EID data by adjusting a pile-up correction applied to a photon count detected at a PC sensor of the layer of PC sensors based on both PC data energy spectrum and an incident flux rate detected at an EID detector positioned at an opposite side of the layer of PC sensors as an incoming x-ray.

6. The CT detector system of claim 1, wherein boundaries between each PC sensor of the number of PC sensors are not aligned with boundaries between each EID detector of the number of EID detectors.

7. The CT detector system of claim 1, further comprising readout electronics positioned at an opposite side of the layer of EID detectors as an incoming x-ray, wherein signals from each PC sensor of the number of PC sensors are transmitted to the readout electronics via wire bonds that are routed between the EID detectors.

8. The CT detector system of claim 1, further comprising a first set of readout electronics and a second set of readout electronics, wherein signals from each EID detector of the number of EID detectors are transmitted to the first set of readout electronics, and signals from each PC sensor of the number of PC sensors are transmitted to the second set of readout electronics.

9. The CT detector system of claim 8, wherein the first set of readout electronics and the second set of readout electronics are positioned at the opposite side of the layer of EID detectors as an incoming x-ray, and signals from each PC sensor of the number of PC sensors are transmitted to the second set of readout electronics via one or more flexible cables routed around the layer of EID detectors.

10. The CT detector system of claim 8, wherein the first set of readout electronics is positioned at the opposite side of the layer of EID detectors as an incoming x-ray, and the second set of readout electronics is positioned to one side of the layer of PC sensors.

11. The CT detector system of claim 10, wherein the PC sensors of the layer of PC sensors are arranged in two-dimensional PC sensor arrays, each PC sensor array including a semiconductor material attached to a printed circuit board (PCB) including a readout electronics of the second set of readout electronics and a plurality of circuits, each circuit of the plurality of circuits electronically coupling a PC sensor of the PC sensor array to the readout electronics.

12. A method for a computed tomography (CT) imaging system, the method comprising:
reconstructing a first image based on photon counting (PC) data received from a PC sensor layer of a CT detector of the CT imaging system;
reconstructing a second image based on energy integration (EI) data received from an EID detector array of the CT detector;
training a convolutional neural network (CNN) to increase a resolution of the second image, using the first image as ground truth data;
combining the first image and the second image to generate a fused image;
inputting the fused image into the trained CNN to generate an output image, the output image having a higher resolution and a lower noise than the fused image; and
displaying the output image on a display device of the CT imaging system, wherein combining the first image and the second image to generate the fused image further comprises weighting the first image by a first parameter and weighting the second image by a second parameter.

13. The method of claim 12, wherein increasing the resolution of the image reconstructed from EID data and PC data using the deep learning CNN trained on pairs of images including a target image reconstructed from a first signal from the layer of PC sensors, and an input image reconstructed from a second signal from the layer of EID detectors further comprises:
creating a fused image from the target image and the input image;
denoising the fused image using at least one of a weighted average method, a guided noise reduction, and a deep learning noise reduction;
inputting the denoised, fused image into the trained CNN to generate an output image, the output image having a higher resolution than the denoised, fused image.

14. The method of claim 12, wherein the EID detector array is positioned at an opposite side of the PC sensor layer as an incoming x-ray.

15. The method of claim 14, wherein boundaries between PC sensors of the PC sensor layer are not aligned with boundaries between EID detectors of the EID detector array.

16. The method of claim 12, wherein the first parameter and the second parameter are selected to perform one of minimizing an amount of noise in the fused image and maximizing a resolution of the fused image.

17. The method of claim 12, further comprising denoising the fused image using at least one of a weighted average method, a guided noise reduction, and a deep learning noise reduction.

18. The method of claim 12, wherein reconstructing the first image based on the PC data received from the PC sensor layer further comprises performing a pile-up correction on photon counts of the PC data, the pile-up correction based on the EID data received from the EID detector array.

19. A computed tomography (CT) detector, comprising:
- a first number of photon counting (PC) sensors arranged in a first layer of the CT detector;
- a second number of energy integrating detectors (EID) arranged in a second layer of the detector, the second layer on an opposite side of the first layer with respect to an incoming x-ray, the second number less than the first number; and
- one or more readout electronics electronically coupled to the first number of PC sensors and the second number of EID detectors, the one or more readout electronics arranged on an opposite side of the second layer with respect to the incoming x-ray, the one or more readout electronics receiving signals from the first number of PC sensors via a plurality of circuits routed along pathways through cast reflectors of the second number of EID detectors or around the second number of EID detectors via a flexible cable.

* * * * *